(12) United States Patent
Schaffer et al.

(10) Patent No.: US 10,996,231 B2
(45) Date of Patent: May 4, 2021

(54) CERAMIDES FOR EVALUATING RISK OF CARDIOVASCULAR DISEASE

(71) Applicants: Washington University, St. Louis, MO (US); Trustees of Boston University, Boston, MA (US)

(72) Inventors: Jean E. Schaffer, Saint Louis, MO (US); Daniel S. Ory, Saint Louis, MO (US); Linda Peterson, Saint Louis, MO (US); Vasan S. Ramachandran, Boston, MA (US); Vanessa Xanthakis, Boston, MA (US)

(73) Assignees: Washington University, St. Louis, MO (US); Trustees of Boston University, Boston, MA (US)

( * ) Notice: Subject to any disclaimer, the term of this patent is extended or adjusted under 35 U.S.C. 154(b) by 0 days.

(21) Appl. No.: 15/536,460

(22) PCT Filed: Dec. 16, 2015

(86) PCT No.: PCT/US2015/066159
§ 371 (c)(1),
(2) Date: Jun. 15, 2017

(87) PCT Pub. No.: WO2016/100549
PCT Pub. Date: Jun. 23, 2016

(65) Prior Publication Data
US 2019/0101550 A1     Apr. 4, 2019

Related U.S. Application Data

(60) Provisional application No. 62/092,392, filed on Dec. 16, 2014.

(51) Int. Cl.
| | | |
|---|---|---|
| *G01N 33/92* | (2006.01) | |
| *G01N 33/49* | (2006.01) | |
| *G01N 30/72* | (2006.01) | |
| *G01N 33/68* | (2006.01) | |
| *G01N 30/02* | (2006.01) | |

(52) U.S. Cl.
CPC ......... *G01N 33/92* (2013.01); *G01N 30/7233* (2013.01); *G01N 33/6893* (2013.01); *G01N 33/49* (2013.01); *G01N 2030/027* (2013.01); *G01N 2405/08* (2013.01); *G01N 2800/2871* (2013.01); *G01N 2800/324* (2013.01)

(58) Field of Classification Search
CPC .... G01N 33/49; G01N 33/92; G01N 30/7233; G01N 2405/08; G01N 2030/027; G01N 2800/2871; G01N 2800/32; G01N 2800/324; G01N 2800/325; Y10T 436/24
USPC .......... 436/63, 71, 161, 173; 435/29
See application file for complete search history.

(56) References Cited

U.S. PATENT DOCUMENTS

| | | | |
|---|---|---|---|
| 2011/0034419 A1 | 2/2011 | Argraves et al. | |
| 2013/0023054 A1 | 1/2013 | Meikle et al. | |
| 2013/0045217 A1 | 2/2013 | Laaksonen et al. | |
| 2015/0362513 A1* | 12/2015 | Laaksonen | G01N 33/92 |
| | | | 506/12 |
| 2017/0160264 A1* | 6/2017 | Sysi-Aho | G01N 33/492 |
| 2018/0306797 A1* | 10/2018 | Schaffer | G01N 33/6893 |

FOREIGN PATENT DOCUMENTS

| | | | |
|---|---|---|---|
| WO | 2011/063470 A1 † | 6/2011 | |
| WO | 2013/014286 A2 † | 1/2013 | |
| WO | 2013/068374 * | 5/2013 | |
| WO | 2013/068374 A2 † | 5/2013 | |
| WO | WO 2013/068373 A2 | 5/2013 | |

OTHER PUBLICATIONS

Chavez, Summers (2012)—A ceramide-centric view of insulin resistance, Cell Metabolism, 15, 5, pp. 585-594.
Cupples, D'Agostino (1987)—Some risk factors related to the annual incidence of cardiovascular disease and death using pooled repeated biennial measurements: Framingham Heart Study, 30-year follow-up, The Framingham Study: An Epidemiological Investigation of Cardiovascular Disease. Section 34. DHHS publication No. (NIH) 87-2703, pp. 1-26.
De Mello et al. (2009)—Link between plasma ceramides, inflammation and insulin resistance: Association with serum IL-6 concentration in patients with coronary heart disease, Diabetologia, 52, 12, pp. 2612-2615.
Dörr et al. (2005)—The Association of Thyroid Function with Cardiac Mass and Left Ventricular Hypertrophy, The Journal of Clinical Endocrinology & Metabolism, 90, 2, pp. 673-677.
Drosatos, Schulze (2013)—Cardiac Lipotoxicity: Molecular Pathways and Therapeutic Implications, Current Heart Failure Reports, 10, 2, pp. 109-121.
Food and Drug Administration (2001)—Guidance for Industry: Bioanalytical Method Validation, U.S. Department of Health and Human Services, pp. 1-22. www.fda.gov/downloads/Drugs/Guidances/ucm070107.pdf.
Haus et al. (2009)—Plasma ceramides are elevated in obese subjects with type 2 diabetes and correlate with the severity of insulin resistance, Diabetes, 58, 2, pp. 337-343.
Ichi et al. (2006)—Association of ceramides in human plasma with risk factors of atherosclerosis, Lipids, 41, 9, pp. 859-863.
International Search Report and Written Opinion dated Feb. 25, 2016 in corresponding International Application No. PCT/US15/66159 filed Dec. 16, 2015, 9 pages.
Jiang et al. (2013)—Development and validation of LC-MS/MS method for determination of very long acyl chain (C22:0 and C24:0) ceramides in human plasma, Analytical and Bioanalytical Chemistry, 405, 23, pp. 7357-7365.
Kasumov et al. (2015)—Improved insulin sensitivity after exercise training is linked to reduced plasma C14:0 ceramide in obesity and type 2 diabetes, Obesity, 23, 7, pp. 1414-1421.

(Continued)

Primary Examiner — Maureen Wallenhorst

(57) ABSTRACT

The present disclosure provides the use of two very long chain ceramides for determining the risk of cardiovascular disease.

24 Claims, 9 Drawing Sheets

(56) References Cited

OTHER PUBLICATIONS

Pan et al. (2014)—Elevation of ceramide and activation of secretory acid sphingomyelinase in patients with acute coronary syndromes, Coronary Artery Disease, 25, 3, pp. 230-235.

Saleem et al. (2013)—Ceramides predict verbal memory performance in coronary artery disease patients undertaking exercise: A prospective cohort pilot study, BMC Geriatrics, 13, 1.

Spijkers et al. (2011)—Hypertension is associated with marked alterations in sphingolipid biology: A potential role for ceramide, PLoS One, 6, 7, pp. 1-9.

Tarasov et al. (2014)—Molecular lipids identify cardiovascular risk and are efficiently lowered by simvastatin and PCSK9 deficiency, Journal of Clinical Endocrinology and Metabolism, 99, 1, pp. 45-52.

Yu et al. (2015)—Ceramide is Upregulated and Associated With Mortality in Patients With Chronic Heart Failure, Canadian Journal of Cardiology, 31, 3, pp. 357-363.

Sigruener et al., Glycerophospholipid and Sphingolipid Species and Mortality: the Ludwigshafen Risk and Cardiovascular Health (LURIC) Study, 2014, Plos One, 9(1):e85724, pp. 1-8.†

DeMello et al., Link between plasma ceramides, inflammation and insulin resistance: association with serum IL-6 concentration in patients with coronary heart disease, 2009, Diabetologia, 52:2612-15.†

Eliasson et al., Clinical Usefulness of Different Lipid Measures for Prediction of Coronary Heart Disease in Type 2 Diabetes, 2011, 34:2095-100.†

Miekle et al., Serum ceramides increase the risk of Alzheimer disease, 2012, Neurology, 79:633-41.†

\* cited by examiner
† cited by third party

CERAMIDES FOR EVALUATING RISK OF CARDIOVASCULAR DISEASE

CROSS REFERENCE TO RELATED APPLICATIONS

The present application claims the benefit of priority to PCT International Application No. PCT/US15/66159, filed Dec. 16, 2015, which claims the benefit of U.S. Provisional Application No. 62/092,392, filed Dec. 16, 2014, each of which is hereby incorporated by reference in its entirety.

GOVERNMENTAL RIGHTS

This invention was made with government support under P20 HL113444 awarded by the NIH. The government has certain rights in the invention.

FIELD OF THE INVENTION

The present disclosure provides the use of two very long chain ceramides for determining the risk of cardiovascular disease.

BACKGROUND OF THE INVENTION

Cardiovascular disease (CVD) is the leading cause of death in the developed world. Clinical manifestations of CVD include myocardial infarction (MI), stroke, sudden death, angina, and heart failure (HF). Epidemiological studies have identified risk factors for CVD, including hypercholesterolemia, smoking, hypertension, diabetes and positive family history of early myocardial infarction. Nonetheless, cardiovascular events can occur in patients without these risk factors, and cardiovascular events can occur in patients who are aggressively treated for established CVD. Because CVD can be fatal upon first presentation, effective primary prevention of CVD requires identification of significant risk factors, followed by intervention to modify risk. This strategy has been very effective with respect to hypercholesterolemia, which can be detected by a blood test—a fasting lipid profile. The risk can be mitigated by employing drug therapy with a cholesterol-lowering agent, such as a statin.

In addition to cholesterol other lipids have been proposed to lead to cardiac dysfunction. One lipid class proposed to be toxic are ceramides, which have been implicated in inflammatory (Chavez and Summers 2012) and apoptosis pathways (Drostos and Schulze). Several previous studies have observed increased incidence of adverse events with increasing ceramide levels (Saleem et al., Ichi et al.). Previous studies have examined ceramide levels by determining the ratios of specific ceramides to other ceramides, their sphingolipid precursors, or other serum lipids (see Ichi et al., Tarasov et al., published US application 2011/0034419 of Argraves et al., or published PCT application WO 2013/068373 of Zora Biosciences OY).

There are contributors to CVD independent of traditional risk factors. Cardiovascular events can occur in patients without traditional risk factors, and cardiovascular events can occur in patients who are aggressively treated for established CVD risk factors. Thus, new prognostic indicators are needed.

SUMMARY OF THE INVENTION

In one aspect, the disclosure provides a method to determine if a subject is at risk of cardiovascular disease (CVD) comprising: measuring the amount of ceramide 24:0, and optionally ceramide 22:0, in a biological sample obtained from the subject; comparing the amount of ceramide 24:0, and optionally ceramide 22:0, in the biological sample to a reference value; and classifying the subject as at risk for CVD if the amount of ceramide 24:0, and optionally ceramide 22:0, is less than the reference value.

In another aspect, the disclosure provides a method to prevent cardiovascular disease (CVD) in a subject comprising: measuring the amount of ceramide 24:0, and optionally ceramide 22:0, in a biological sample obtained from the subject; comparing the amount of ceramide 24:0, and optionally ceramide 22:0, in the biological sample to a reference value; classifying the subject as at risk for CVD if the amount of ceramide 24:0, and optionally ceramide 22:0, is less than the reference value; and treating the subject to prevent future CVD events when the subject is at risk for CVD.

In still another aspect, the disclosure provides a method for monitoring cardiovascular disease (CVD) in a subject comprising: measuring the amount of ceramide 24:0, and optionally ceramide 22:0, in a biological sample obtained from the subject; and then at a later time, measuring the amount of ceramide 24:0, and optionally ceramide 22:0, in a biological sample obtained from the subject, wherein a change in ceramide 24:0, and optionally ceramide 22:0, indicates a change in risk of the subject over time.

BRIEF DESCRIPTION OF THE FIGURES

(FIG. 1A, FIG. 1B, FIG. 1C, FIG. 1D) Cumulative incidence of (FIG. 1A) cardiovascular disease (CVD), (FIG. 1B) coronary heart disease (CHD), (FIG. 1C) heart failure (HF), and (FIG. 1D) all-cause mortality are reported for tertiles of C22:0 ceramide. (FIG. 1E, FIG. 1F, FIG. 1G, FIG. 1H) Cumulative incidence of (FIG. 1E) cardiovascular disease (CVD), (FIG. 1F) coronary heart disease (CHD), (FIG. 1G) heart failure (HF), and (FIG. 1H) all-cause mortality are reported for tertiles of C24:0 ceramide. Tertile 1 includes participants with ceramide levels≤the $33^{rd}$ percentile; tertile 2 includes participants with ceramide levels between the $33^{rd}$ and $66^{th}$ percentile; tertile 3 includes participants with ceramide levels≥the $66^{th}$ percentile.

(FIG. 4A, FIG. 4B) Plots display distribution of values for (FIG. 4A) C22:0 and (FIG. 4B) C24:0 ceramides in FHS Offspring cohort at examination 8. (FIG. 4C, FIG. 4D) Plots display distribution of values for (FIG. 4C) C22:0 and (FIG. 4D) C24:0 ceramides in SHIP participants at SHIP-1 examination.

DETAILED DESCRIPTION OF THE INVENTION

Figure 1A:
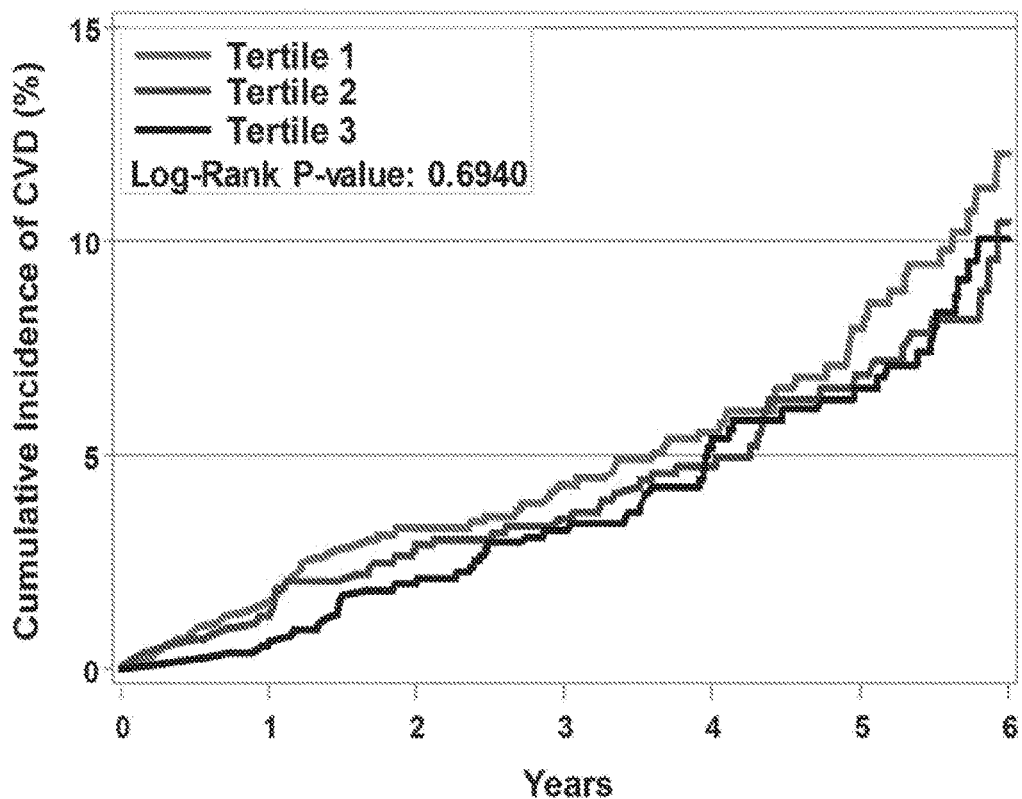
FIG. 1A, FIG. 1B, FIG. 1C, FIG. 1D, FIG. 1E, FIG. 1F, FIG. 1G and FIG. 1H depict graphs showing the cumulative incidence of cardiovascular disease and mortality by tertiles of ceramides.
Figure 1B:
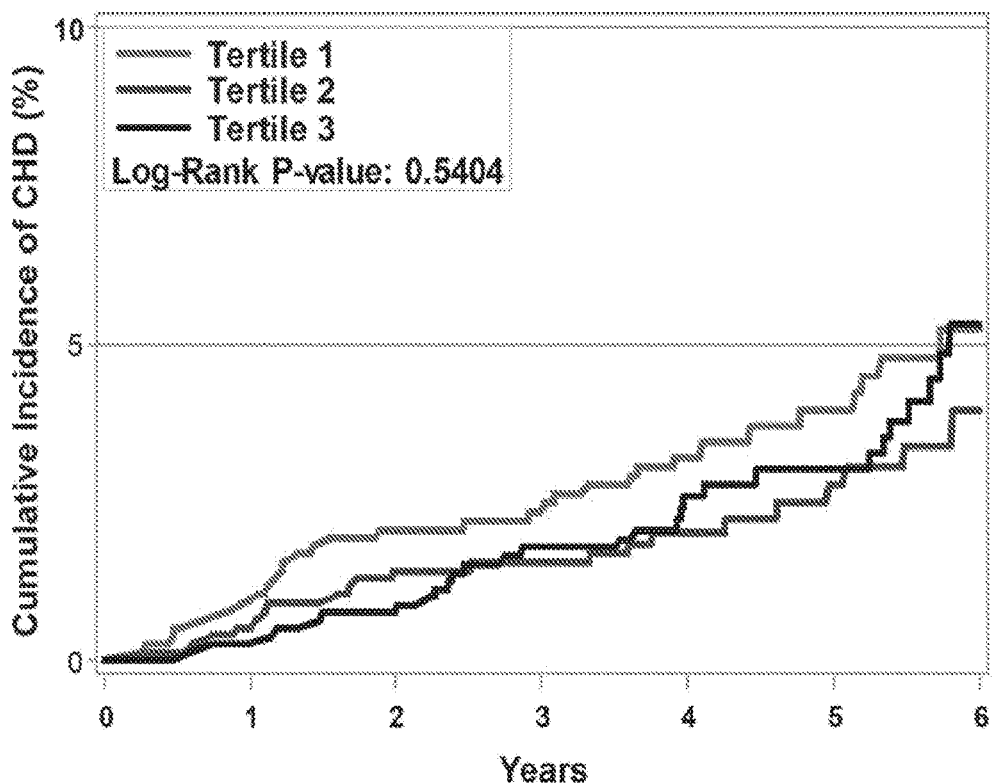
Figure 1C:
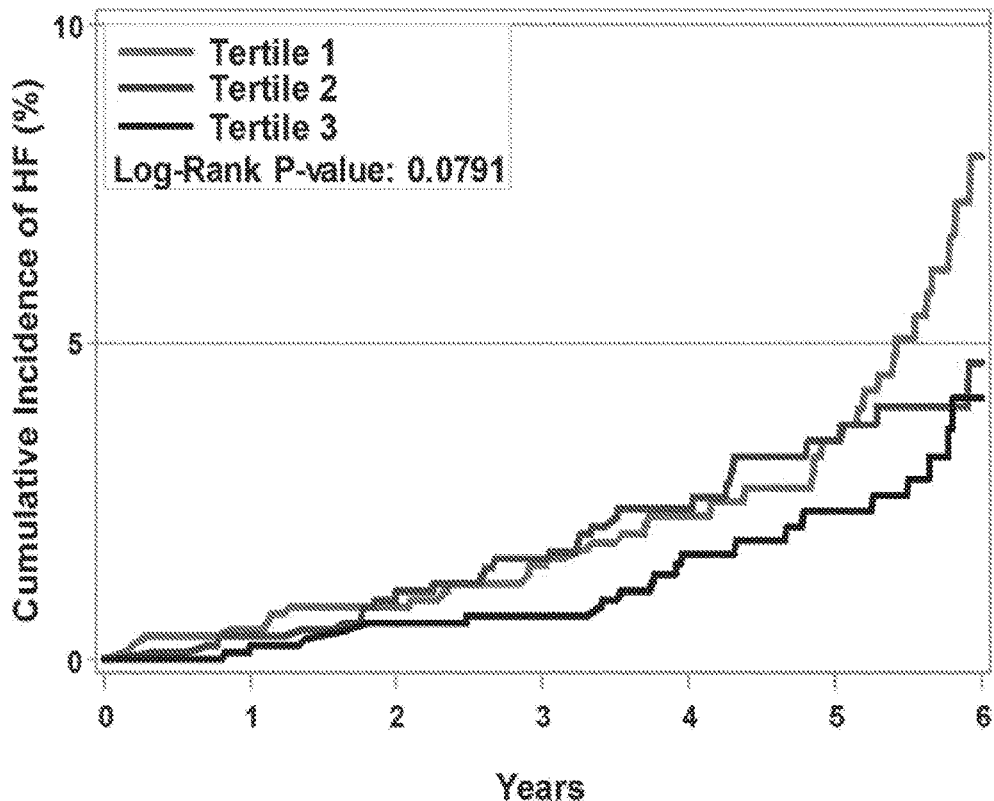
Figure 1D:
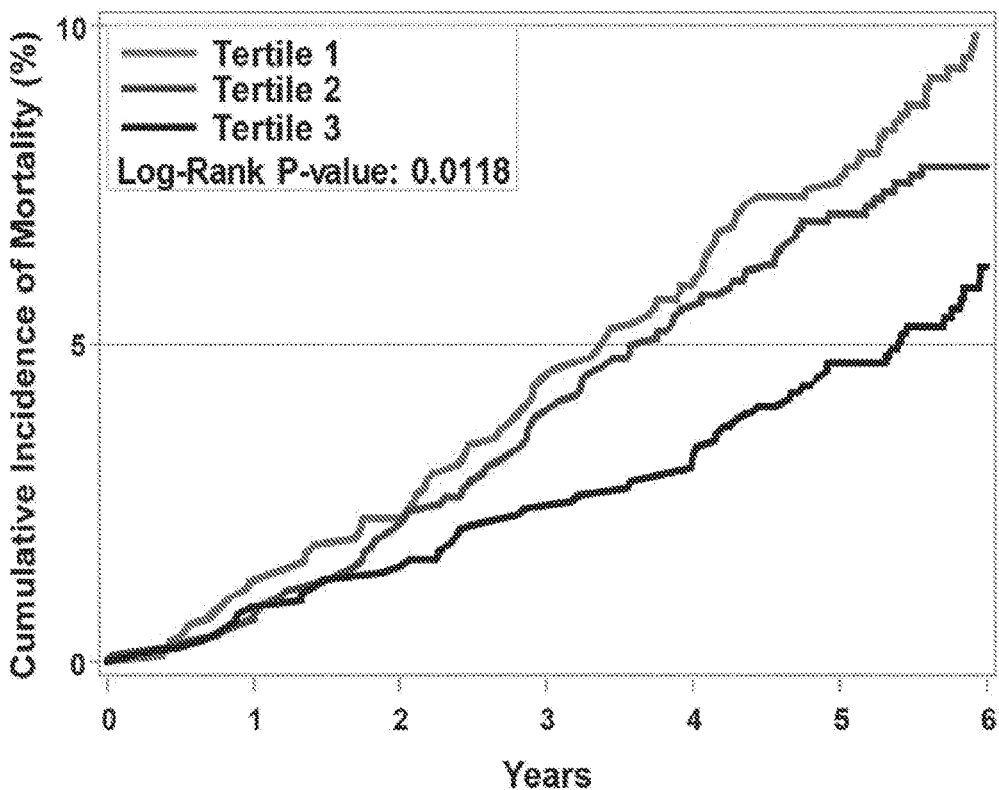
Figure 1E:
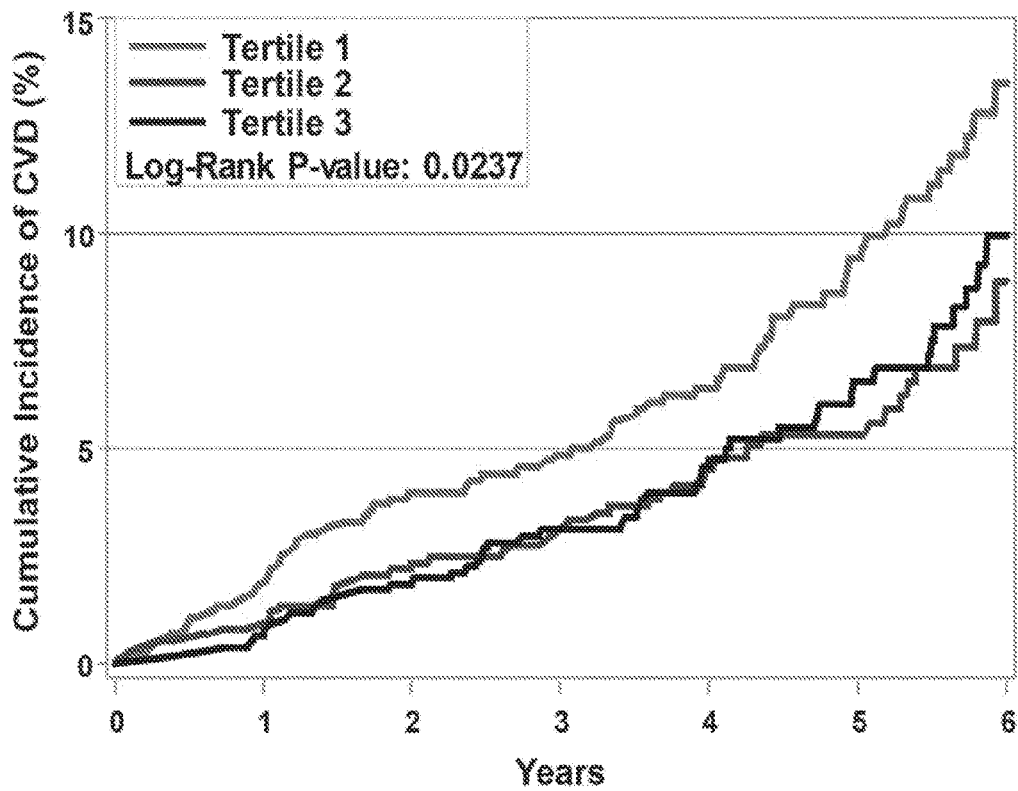
Figure 1F:
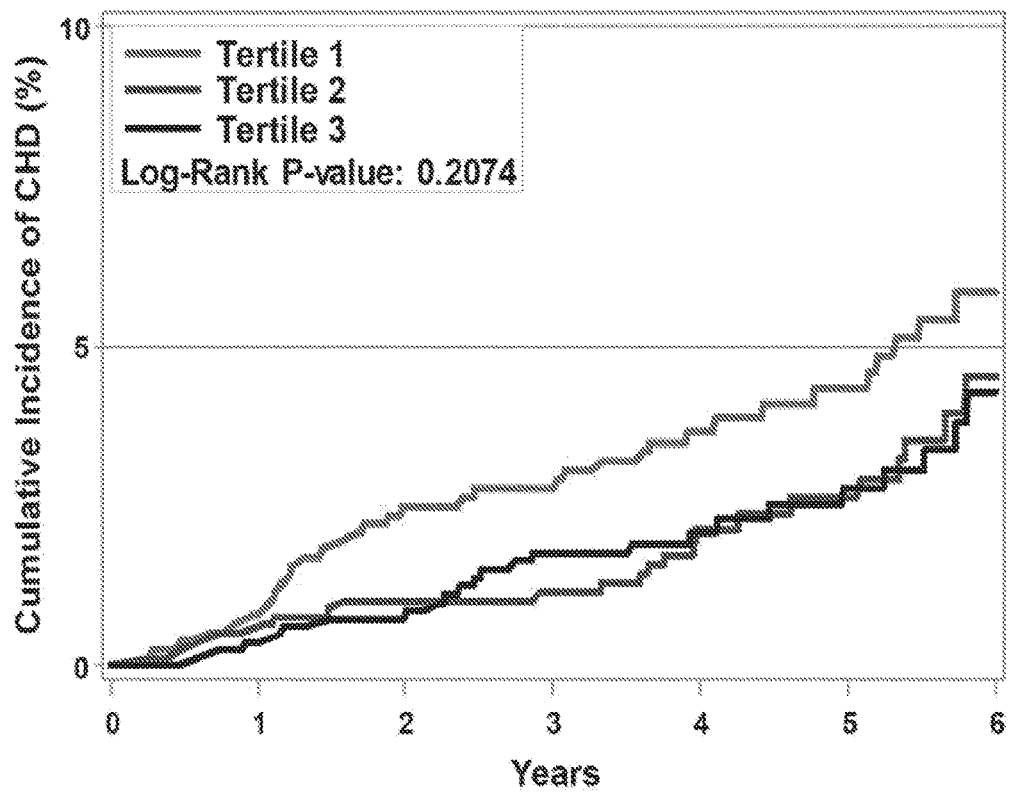
Figure 1G:
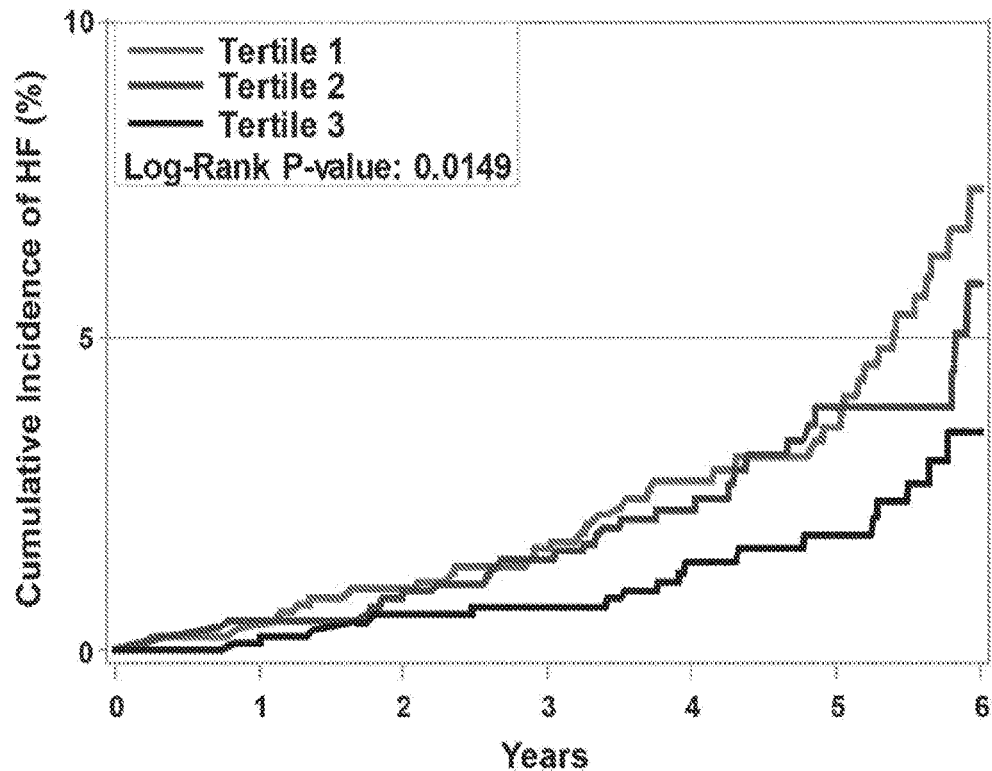
Figure 1H:
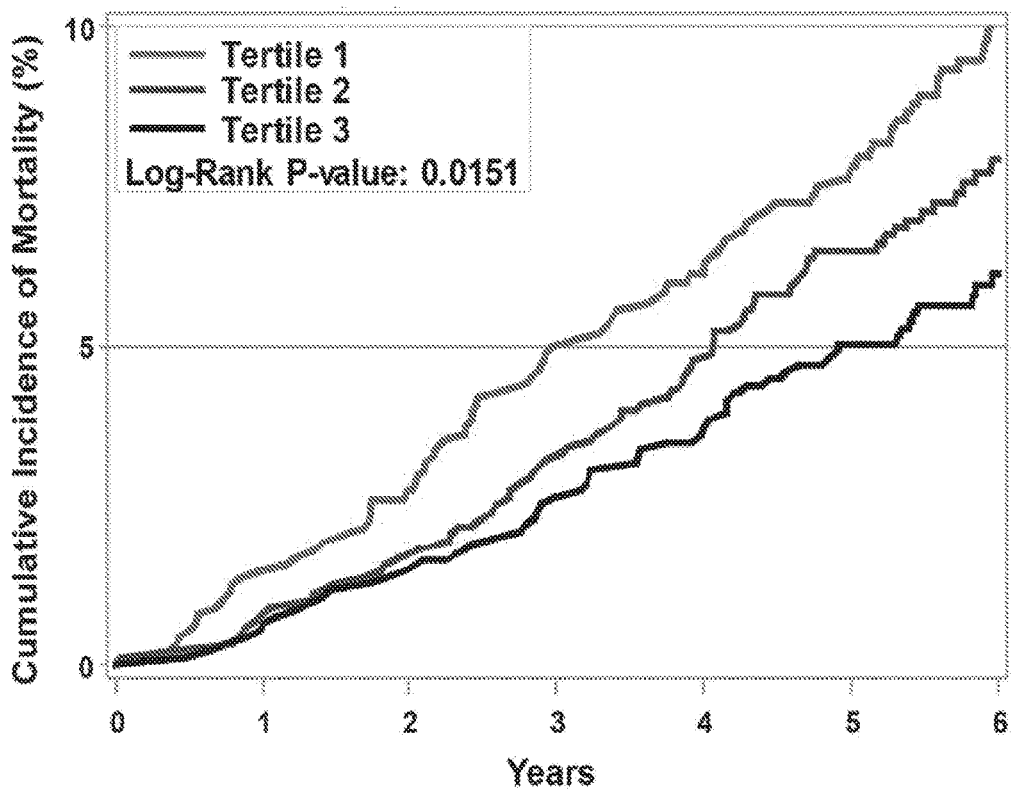
Figure 2A:
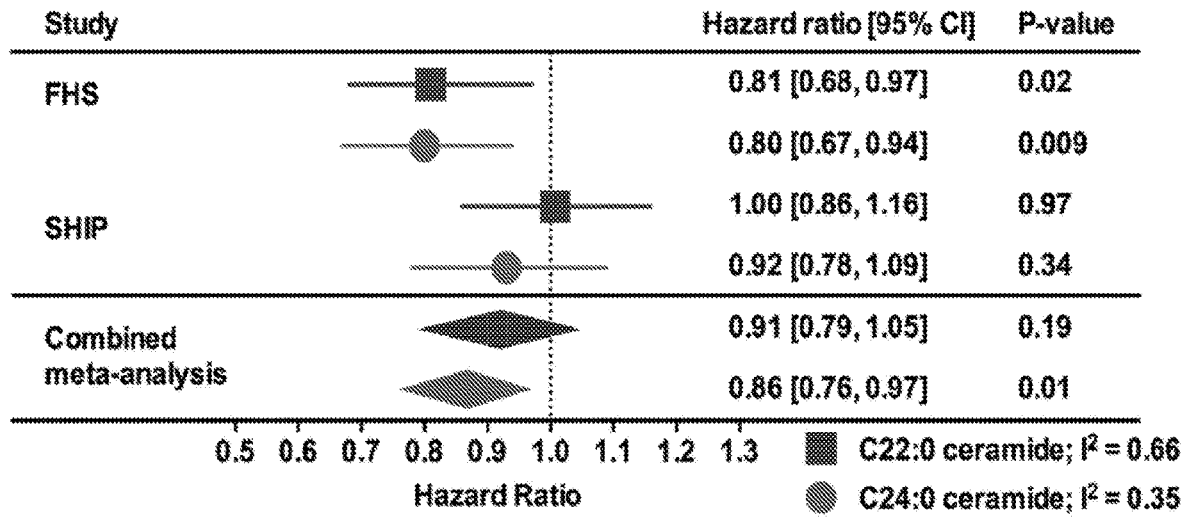
FIG. 2A, FIG. 2B, FIG. 2C and FIG. 2D depict the risk of cardiovascular disease and mortality by ceramide level. Hazard ratios for (FIG. 2A) cardiovascular disease (CVD), (FIG. 2B) coronary heart disease (CHD), (FIG. 2C) heart failure (HF), and (FIG. 2D) all-cause mortality are reported with 95% confidence intervals (CI) for each standard deviation increase C22:0 and C24:0 ceramide. Data are shown from analysis of subjects in the Framingham Heart Study (FHS), the Study of Health in Pomerania (SHIP) and the combined meta-analysis.
Figure 2B:
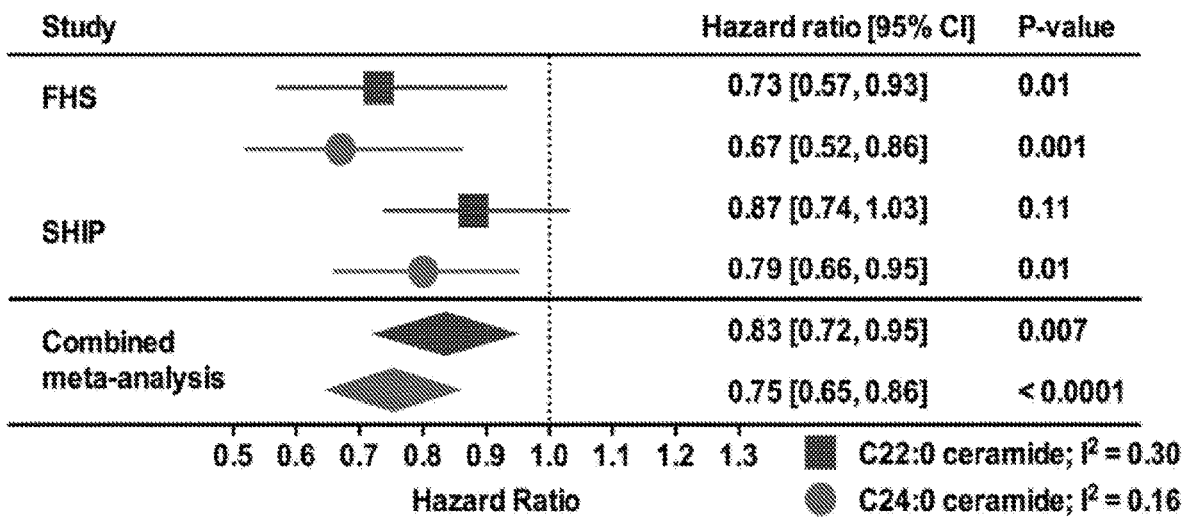
Figure 2C:
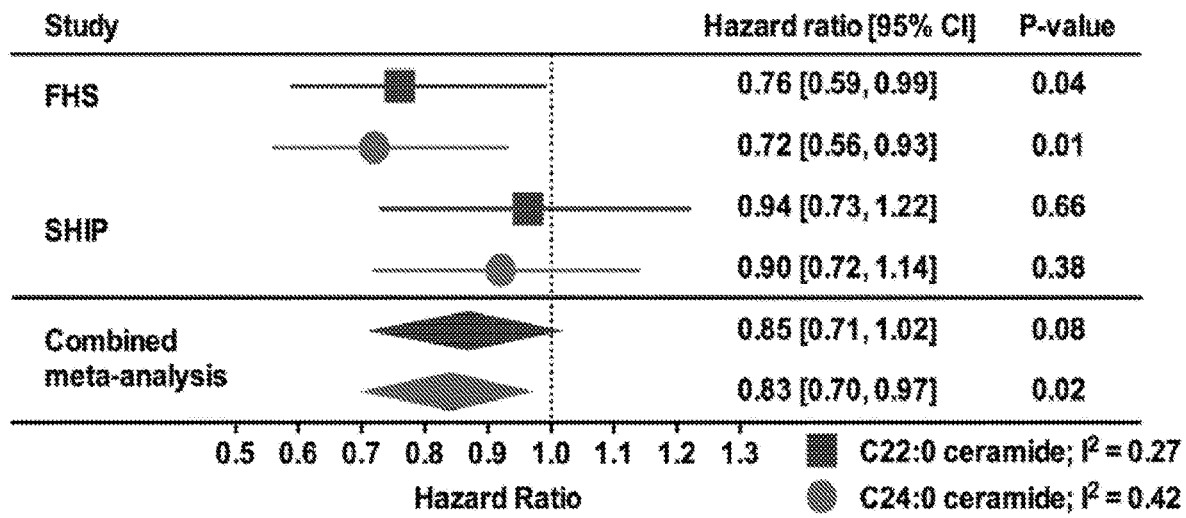
Figure 2D:
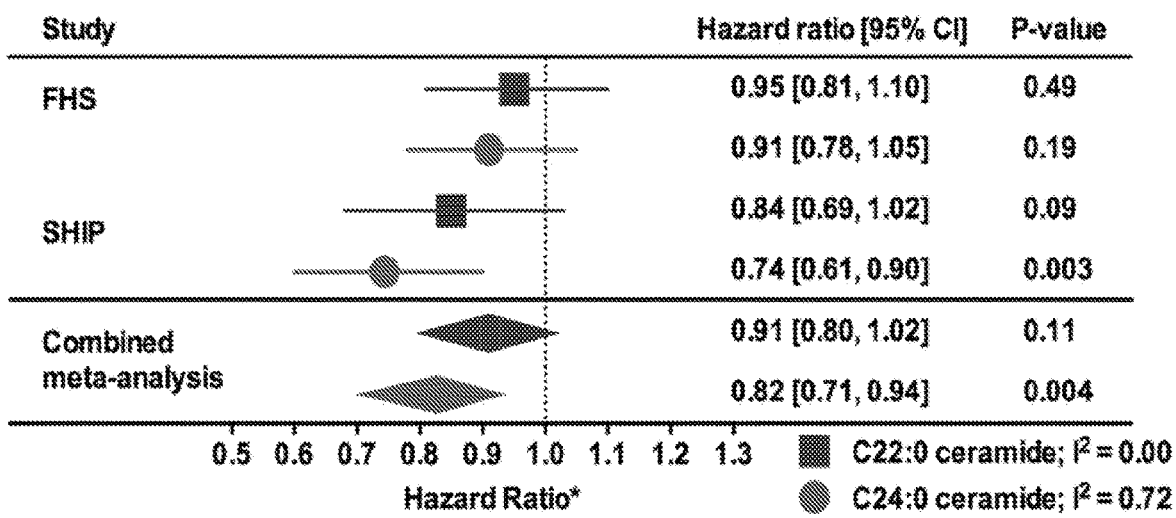

The present disclosure provides a statistically significant relationship between increases in blood concentrations of identified ceramide species and decreases in incidence of cardiovascular disease (CVD). It was unexpected that increased levels of these ceramide species would correlate with a decreased risk of developing CVD. These results are opposite of the effects observed in previous studies (Saleem et al., 2013; Ichi et al., 2006). Accordingly, provided herein are methods that utilize this relationship to provide inventive means of assessing the risk of progression to CVD.

Specifically, the ceramide species are two very long chain species: C22:0 ceramide and C24:0 ceramide. Ceram ides are a family of waxy lipid molecules. Ceramides consist of a long-chain or sphingoid base linked to a fatty acid via an amide bond. C22:0 ceramide may also be referred to as d18:1/22:0 and C24:0 ceramide may also be referred to as d18:1/24:0.

Provided herein are methods for detecting C22:0 and C24:0 ceramide and their use in classifying a subject at risk for CVD. Various aspects of these methods are described in more detail below.

I. Methods

In an aspect, the disclosure provides a method to classify a subject based on the amount of ceramide 24:0, and optionally ceramide 22:0, measured in a biological sample obtained from the subject. The method generally comprises (i) measuring the amount of ceramide 24:0, and optionally ceramide 22:0, in the biological sample, (ii) comparing the amount of ceramide 24:0, and optionally ceramide 22:0, in the biological sample to a reference value, and (iii) classifying the subject as having an increased or decreased amount of ceramide 24:0, and optionally ceramide 22:0, based on the amount of ceramide 24:0, and optionally ceramide 22:0, measured in the sample. In an embodiment, both ceramide 24:0 and ceramide 22:0 are measured.

In another aspect, the disclosure provides a method to determine if a subject is at risk of cardiovascular disease (CVD). The method generally comprises (i) measuring the amount of ceramide 24:0, and optionally ceramide 22:0, in a biological sample obtained from the subject, (ii) comparing the amount of ceramide 24:0, and optionally ceramide 22:0, in the biological sample to a reference value, and (iii) classifying the subject as at risk for CVD if the amount of ceramide 24:0, and optionally ceramide 22:0, is less than the reference value. In an embodiment, both ceramide 24:0 and ceramide 22:0 are measured. The subject may have no other risk factors for CVD. Alternatively, the subject may have one or more risk factors for CVD. Non-limiting examples of risk factors for CVD include family history, ethnicity, age, sex, body mass index (BMI), tobacco exposure, high blood pressure (hypertension), high cholesterol, obesity, physical inactivity, diabetes, unhealthy diet, harmful use of alcohol, poverty, stress, social isolation, anxiety, depression, use of contraceptive pill, use of hormone replacement therapy, prior CVD, and left ventricular hypertrophy (LVH). Specifically, the CVD is coronary heart disease (CHD) or heart failure (HF). Additionally, the CVD includes fatal and non-fatal CHD, cerebrovascular disease (stroke or transient ischemic attack), peripheral arterial disease (intermittent claudication) and heart failure. CHD includes myocardial infarction (MI), coronary insufficiency and angina pectoris.

In still another aspect, the disclosure provides a method to prevent cardiovascular disease (CVD) in a subject. The method generally comprises (i) measuring the amount of ceramide 24:0, and optionally ceramide 22:0, in a biological sample obtained from the subject, (ii) comparing the amount of ceramide 24:0, and optionally ceramide 22:0, in the biological sample to a reference value, (iii) classifying the subject as at risk for CVD if the amount of ceramide 24:0, and optionally ceramide 22:0, is less than the reference value, and (iv) treating the subject to prevent future CVD events. In an embodiment, both ceramide 24:0 and ceramide 22:0 are measured. The subject may have no history of CVD. Alternatively, the subject may have a history of CVD. Specifically, the CVD is coronary heart disease (CHD) or heart failure (HF). Additionally, the CVD includes fatal and non-fatal CHD, cerebrovascular disease (stroke or transient ischemic attack), peripheral arterial disease (intermittent claudication) and heart failure. CHD includes myocardial infarction (MI), coronary insufficiency and angina pectoris. Treatment may consist of standard treatments for CVD. Non-limiting examples of standard treatment for CVD include stress reduction, diet changes, lifestyle changes, drugs and surgery. Non-limiting examples of lifestyle changes include cessation of smoking, exercising, alcohol in moderation, and relaxation techniques such as mediation, progressive relaxation, yoga and biofeedback training. Non-limiting examples of diet changes include lowering sodium and trans fat consumption and increasing intake of fresh fruits and vegetables, whole unprocessed high-fiber grains, and healthy sources of fats and proteins. Non-limiting examples of drugs include aspirin, ACE inhibitors, angiotensin II receptor blockers, anti-arrhythmics, beta-blockers, high blood pressure medication, high cholesterol medication, diuretics, water pills, calcium channel blocker drugs, thrombolytic drugs, digoxin, nitrates, hydralazine, antiplatelet drugs, blood thinners, and corticosteroids. Non-limiting examples of percutaneous interventions and surgery include balloon angioplasty and stents, balloon valvuloplasty, heart bypass surgery, open heart surgery, pacemaker or defibrillator implantation, heart transplantation, cardioconversion, atrial fibrillation and bypass tract ablation and left ventricular assist device (LVAD).

In still yet another aspect, the disclosure provides a method for monitoring cardiovascular disease (CVD) in a subject. In such an embodiment, a method of detecting ceramide 24:0, and optionally ceramide 22:0, may be used to assess the risk of a subject at one point in time. Then at a later time, the method of detecting ceramide 24:0, and optionally ceramide 22:0, may be used to determine the change in risk of the subject over time. For example, the method of detecting ceramide 24:0, and optionally ceramide 22:0, may be used on the same subject days, weeks, months or years following the initial determination of the amount of ceramide 24:0, and optionally ceramide 22:0. Accordingly, the method of detecting ceramide 24:0, and optionally ceramide 22:0, may be used to follow a subject over time to determine when the risk of progressing to more severe disease is high thereby requiring treatment. Additionally, the method of detecting ceramide 24:0, and optionally ceramide 22:0, may be used to measure the rate of disease progression. For example, an increased amount of ceramide 24:0, and optionally ceramide 22:0, may indicate an abatement of disease progression. Alternatively, a decreased amount of ceramide 24:0, and optionally ceramide 22:0, may indicate disease progression. In an embodiment, both ceramide 24:0 and ceramide 22:0 are measured.

Additionally, a method for monitoring cardiovascular disease (CVD) in a subject may also be used to determine the response to treatment. As used herein, subjects who respond to treatment are said to have benefited from treatment. Responses to treatment are measured in clinical practice using tests including, but not limited to, blood pressure test, LDL cholesterol test, chest X-ray, electrocardiogram (ECG), Holter monitoring, echocardiogram, stress test, blood test, cardiac catheterization, electrophysiology test, CT heart scan, myocardial biopsy, heart MRI, and pericardiocentesis. These tests are well known in the art and are intended to refer to specific parameters measured during clinical trials and in clinical practice by a skilled artisan. For example, a method to detect ceramide 24:0, and optionally ceramide 22:0, may be performed on the biological sample of the subject prior to initiation of treatment. Then at a later time, a method to detect ceramide 24:0, and optionally ceramide 22:0, may be used to determine the response to treatment over time. For example, a method to detect ceramide 24:0, and optionally ceramide 22:0, may be performed on the biological sample of the same subject days, weeks, months or years following initiation of treatment. Accordingly, a method to detect ceramide 24:0, and optionally ceramide 22:0, may be used to follow a subject receiving treatment to determine if the subject is responding to treatment. If the amount of ceramide 24:0, and optionally ceramide 22:0, increases, then the subject may be responding to treatment. If the amount of ceramide 24:0, and optionally ceramide 22:0, decreases or remains the same, then the subject may not be responding to treatment. These steps may be repeated to determine the response to therapy over time.

By "cardiovascular disease" is meant a class of diseases that involve the heart or blood vessels. CVD includes, but is not limited to, coronary artery diseases (CAD) [also known as coronary heart disease (CHD) and ischemic heart disease] such as angina pectoris, coronary insufficiency, and myocardial infarction (heart attack), peripheral arterial disease (intermittent claudication), cerebrovascular disease (such as stroke or transient ischemic attack), renal artery stenosis, aortic aneurysm, cardiomyopathy, hypertensive heart disease, heart failure, pulmonary heart disease, cardiac dysrhythmias (such as atrial fibrillation), inflammatory heart disease (such as endocarditis, inflammatory cardiomegaly, and myocarditis), valvular heart disease, rheumatic heart disease, congenital heart disease, and venous thrombosis.

Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. In a preferred embodiment, the subject is human.

A subject may or may not be having a symptom associated with CVD. Specifically, the CVD may be coronary heart disease (CHD) or heart failure (HF). Additionally, the CVD includes fatal and non-fatal CHD, cerebrovascular disease (stroke or transient ischemic attach), peripheral arterial disease (intermittent claudication) and heart failure. CHD includes myocardial infarction (MI), coronary insufficiency and angina pectoris. A skilled artisan will appreciate that pathological CVD likely commences prior to diagnosis or the onset of symptoms associated with CVD. In some embodiments, a subject is having a symptom associated with CVD. In other embodiments, a subject is not having a symptom associated with CVD. In still other embodiments, a subject has detectable CVD but is not having any other symptom associated with CVD. In yet still other embodiments, a subject has received treatment for CVD. Early assessment of the risk of CVD in the subject may reduce the development and/or progression of symptoms associated with the pathological CVD by enabling improved interventions or enabling earlier interventions.

Exemplary symptoms associated with CVD include, but are not limited to, angina or chest pain (discomfort, heaviness, pressure, aching, burning, fullness, squeezing, or painful feeling in your chest); shortness of breath; heart palpitations; faster heartbeat; weakness or dizziness; nausea; sweating; discomfort, pressure, heaviness, or pain in the arm or below the breastbone; discomfort radiating to the back, jaw, throat, or arm; fullness, indigestion or choking feeling; vomiting; anxiety; rapid or irregular heart; lack of energy; swelling of ankles or feet; swelling in abdomen; quick weight gain; cough that produces white sputum; and limited ability to exercise.

As used herein, the term "biological sample" refers to a sample obtained from a subject. Any biological sample containing ceramides is suitable. Numerous types of biological samples are known in the art. Suitable biological sample may include, but are not limited to, tissue samples or bodily fluids. In some embodiments, the biological sample is a tissue sample such as a tissue biopsy. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a ceramide extract. In other embodiments, the sample may be a bodily fluid. Non-limiting examples of suitable bodily fluids include blood, plasma, serum, urine, and saliva. In a specific embodiment, the biological sample is blood, plasma, or serum. In a specific embodiment, the biological sample is plasma. The fluid may be used "as is", the cellular components may be isolated from the fluid, or a ceramide fraction may be isolated from the fluid using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the ceramides can be accurately detected and the amount measured according to the disclosure.

In some embodiments, a single sample is obtained from a subject to detect ceramide in the sample. Alternatively, ceramide may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 0.5, 1, 2, 3, 4, 5, 6, 7, 8, 9, 10, 11, 12 or more hours. In some embodiments, samples are collected every 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days.

Once a sample is obtained, it is processed in vitro to detect and measure the amount of ceramide. All suitable methods for detecting and measuring an amount of ceramide known to one of skill in the art are contemplated within the scope of the invention. For example, epitope binding agent assays (i.e. antibody assays), enzymatic assays, electrophoresis, chromatography and/or mass spectrometry may be used. Non-limiting examples of epitope binding agent assays include an ELISA, a lateral flow assay, a sandwich immunoassay, a radioimmunoassay, an immunoblot or Western blot, flow cytometry, immunohistochemistry, and an array. In one embodiment, ceramides are detected using mass spectrometry. Ceramides may be detected through direct infusion into the mass spectrometer. In another embodiment, ceramides are detected using chromatography. In particular, techniques linking a chromatographic step with a mass spectrometry step may be used. The chromatographic step may be liquid chromatography, gas chromatography or thin-layer chromatography (TLC). Generally speaking, the presence of ceramides may be determined utilizing liquid chromatography followed by mass spectrometry. In some embodiments, the liquid chromatography is high performance liquid chromatography (HPLC). Non-limiting examples of HPLC include partition chromatography, normal phase chromatography, displacement chromatography, reverse phase chromatography, size exclusion chromatography, ion exchange chromatography, bioaffinity chromatography, aqueous normal phase chromatography or ultrafast liquid chromatography. Non-limiting examples of mass spectrometry include constant neutral loss mass spectrometry, tandem mass spectrometry (MS/MS), matrix-assisted laser desorption/ionization (MALDI), electrospray ionization mass spectrometry (ESI-MS). In a specific embodiment, the method for detecting and measuring the amount of ceramide in a biological sample is liquid chromatography followed by tandem mass spectrometry (LC-MS/MS). More specifically, the method for detecting and measuring the amount of ceramide in a biological sample is as described in Jiang et al., *Anal Bioanal Chem* 2013; 405(23): 7357-7365, the disclosure of which is hereby incorporated by reference in its entirety.

A subject may be classified based on the amount of ceramide 24:0, and optionally ceramide 22:0, measured in the sample. Classifying a subject based on the amount of ceramide 24:0, and optionally ceramide 22:0, measured in a sample of biological fluid obtained from the subject may be used to identify subjects at risk of CVD or in need of prevention of CVD or to monitor the progression of CVD or to monitor the response to treatment for CVD. Generally speaking, a subject may be classified as having an increased or decreased amount of ceramide 24:0, and optionally ceramide 22:0, compared to a reference value, wherein an increased amount of ceramide 24:0, and optionally ceramide 22:0, is an amount above the reference value and a decreased amount is an amount equal to or below the reference value. In preferred embodiments, to classify a subject as having a decreased amount of ceramide 24:0 or ceramide 22:0, the amount of ceramide 24:0 or ceramide 22:0 in the sample compared to the reference value may be at least 1.5% less. For example, the amount of ceramide 24:0 or ceramide 22:0 in the sample may be at least 1.5%, at least 2%, at least 2.5%, at least 3%, at least 3.5%, at least 4%, at least 4.5%, at least 5%, at least 10%, at least 15%, at least 20%, at least 25%, at least 30%, at least 40%, at least 50%, at least 60%, at least 70%, at least 80%, at least 90%, or at least 100% less than the reference value. In other embodiments, the amount of ceramide 24:0 or ceramide 22:0 in the sample of biological fluid obtained from the subject compared to the reference value may be decreased when the ratio of ceramide 24:0 or ceramide 22:0 to reference value is less than 1. For example, the amount of ceramide 24:0 or ceramide 22:0 in the sample compared to the reference value may be decreased when the ratio of ceramide 24:0 or ceramide 22:0 to reference value is less than 1, less than 0.8, less than 0.6, less than 0.4, less than 0.2, less than 0.1, less than 0.05, or less than 0.001. Alternatively, the amount of ceramide 24:0 or ceramide 22:0 in the sample of biological fluid obtained from the subject compared to the reference value may be increased when the ratio of ceramide 24:0 or ceramide 22:0 to reference value is greater than 1. For example, the amount of ceramide 24:0 or ceramide 22:0 in the sample compared to the reference value may be increased when the ratio of ceramide 24:0 or ceramide 22:0 to reference value is greater than 1, greater than 1.2, greater than 1.5, greater than 1.7, greater than 2, greater than 3, greater than 5, greater than 10, greater than 15, or greater than 20. In another embodiment, the increase or decrease in amount of ceramide 24:0 or ceramide 22:0 is measured using p-value. For instance, when using p-value, the amount ceramide 24:0 or ceramide 22:0 is identified as being significantly different from the reference value when the p-value is less than 0.1, preferably less than 0.05, less than 0.01, less than 0.005, or less than 0.001.

Any suitable reference value known in the art may be used. For example, a suitable reference value may be the amount of ceramide in a biological sample obtained from a subject or group of subjects of the same species that has no detectable CVD. In another example, a suitable reference value may be the amount of ceramide in a biological sample obtained from a subject or group of subjects of the same species that has detectable CVD as measured via standard methods. In another example, a suitable reference value may be a measurement of the amount of ceramide in a reference sample obtained from the same subject. The reference sample comprises the same type of biological fluid as the test sample, and may or may not be obtained from the subject when CVD was not suspected. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began. In such an example, a subject may have suspected CVD but may not have other symptoms of CVD or the subject may have suspected CVD and one or more other symptom of CVD. In a specific embodiment, a suitable reference value may be a threshold provided in the Examples. For example, a suitable reference value for ceramide 24:0 may be a value corresponding to 1.97 μg/ml. Alternatively, a suitable reference value for ceramide 24:0 may be a value corresponding to 2.45 μg/ml. Additionally, a suitable reference value for ceramide 22:0 may be a value corresponding to 0.523 μg/ml. Alternatively, a suitable reference value for ceramide 22:0 may be a value corresponding to 0.659 μg/ml.

A decreased amount of ceramide 24:0 relative to a reference value indicates an increased risk in developing CVD. Specifically, a subject has an increased risk of CVD when the amount of ceramide 24:0 is less than 1.97 μg/ml. Alternatively, a subject has an increased risk of CVD when the amount of ceramide 24:0 is less than 2.45 μg/ml. Further, a subject has a decreased risk of CVD when the amount of ceramide 24:0 is greater than 2.45 μg/ml. When ceramide 22:0 is also measured, a decreased amount of ceramide 22:0 relative to a reference value indicates an increased risk in developing CVD. Specifically, a subject has an increased risk of CVD when the amount of ceramide 22:0 is less than 0.523 μg/ml. Alternatively, a subject has an increased risk of CVD when the amount of ceramide 22:0 is less than 0.659 μg/ml. Further, a subject has a decreased risk of CVD when the amount of ceramide 22:0 is greater than 0.659 μg/ml.

Additionally, a subject's risk of developing CVD may be determined by identifying the tertile with which the amount of ceramide measured in the subject falls in to. A subject in the bottom tertile has the highest risk of developing CVD, a subject in the middle tertile has a lower risk of developing CVD and a subject in the top tertile has the least risk of developing CVD. For example, a subject in the bottom tertile can include individuals with a ceramide 24:0 level of less than 1.97 μg/ml. Furthermore, the middle tertile can include individuals with a ceramide 24:0 level of 1.97 μg/ml to 2.45 μg/ml; and the top tertile can include individuals with a ceramide 24:0 level greater than 2.45 μg/ml. Additionally, for ceramide 22:0, the bottom tertile can include individuals with a ceramide 22:0 level lower than 0.523 μg/ml. Furthermore, the middle tertile can include individuals with a ceramide 22:0 level between 0.523 μg/ml and 0.659 μg/ml; and the top tertile can include individuals with a ceramide 22:0 level above 0.659 μg/ml. In various configurations, a subject with a ceramide 24:0 level in the lower tertile can have 1.5-fold increased risk of CVD, and a subject with a ceramide 22:0 in the lower tertile can have 1.2-fold increased risk of CVD.

The term "risk" as used herein refers to the probability that an event will occur over a specific time period. For example, the probability that a CVD event will occur within 6, 12, 18, or 24 months or 3, 4 or 5 years after testing. Risk can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1-p) where p is the probability of event and (1-p) is the probability of no event) to no-conversion.

An increased amount of ceramide 24:0 relative to a reference value may indicate about a 5% to about a 100% decreased risk of developing CVD. For example, an increased amount of ceramide 24:0 relative to a reference value may indicate about a 5% to about a 95%, about a 5% to about a 90%, about a 5% to about a 85%, about a 5% to about a 80%, about a 5% to about a 75%, about a 5% to about a 70%, about a 5% to about a 65%, about a 5% to about a 60%, about a 5% to about a 55%, about a 5% to about a 50%, about a 5% to about a 45%, about a 5% to about a 40%, or about a 5% to about a 35% decreased risk for developing CVD. Specifically, every standard deviation increase in amount of ceramide 24:0 relative to a reference value may correspond to about a 5% to about a 50% decreased risk of developing CVD. For example, every standard deviation increase in amount of ceramide 24:0 relative to a reference value may correspond to about a 5% to about a 50%, about a 5% to about a 45%, about a 5% to about a 40%, about a 5% to about a 35%, about a 10% to about a 50%, about a 10% to about a 45%, about a 10% to about a 40%, about a 10% to about a 35%, about a 15% to about a 50%, about a 15% to about a 45%, about a 15% to about a 40%, or about a 15% to about a 35% decreased risk of developing CVD.

The determination of risk may be used to select treatment for CVD subjects. As explained herein, ceramide 24:0, and optionally ceramide 22:0, can classify a subject as having an increased risk of CVD and into groups that might benefit from therapy. In an embodiment, a subject classified as having an increased risk of CVD may be treated. A skilled artisan would be able to determine standard treatment for CVD. Accordingly, the methods disclosed herein may be used to select treatment for CVD subjects. In an embodiment, the subject is treated based on the difference in amount of ceramides relative to the reference level. This classification may be used to identify groups that are in need of treatment or not or in need of more aggressive treatment. The term "treatment" or "therapy" as used herein means any treatment suitable for the treatment of CVD. Treatment may consist of standard treatments for CVD. Non-limiting examples of standard treatment for CVD include stress reduction, diet changes, lifestyle changes, drugs and surgery. Non-limiting examples of lifestyle changes include cessation of smoking, exercising, alcohol in moderation, and relaxation techniques such as mediation, progressive relaxation, yoga and biofeedback training. Non-limiting examples of diet changes include lowering sodium and trans fat consumption and increasing intake of fresh fruits and vegetables, whole unprocessed high-fiber grains, and healthy sources of fats and proteins. Non-limiting examples of drugs include aspirin, ACE inhibitors, angiotensin II receptor blockers, anti-arrhythmics, beta-blockers, high blood pressure medication, high cholesterol medication, diuretics, water pills, calcium channel blocker drugs, thrombolytic drugs, digoxin, nitrates, hydralazine, antiplatelet drugs, blood thinners, and corticosteroids. Non-limiting examples of percutaneous interventions and surgery include balloon angioplasty and stents, balloon valvuloplasty, heart bypass surgery, open heart surgery, pacemaker or defibrillator implantation, heart transplantation, cardioconversion, atrial fibrillation and bypass tract ablation and left ventricular assist device (LVAD).

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Association Between Ceramides and Standard Risk Factors in Framingham Heart Study (FHS)

The goal of the study was to determine whether specific ceramide molecular species are associated with the incidence of CVD (including coronary heart disease [CHD] and heart failure [HF]) and all-cause mortality. Whether the absolute levels of a single molecular species of ceramide in plasma is associated with the risk of CVD or all-cause mortality in an unselected sample of the general population is not known. To address this question, plasma levels of very long chain ceramides were related to the risk of CVD, CHD, HF, and all-cause mortality in a large community-based sample.

Figure 4A:
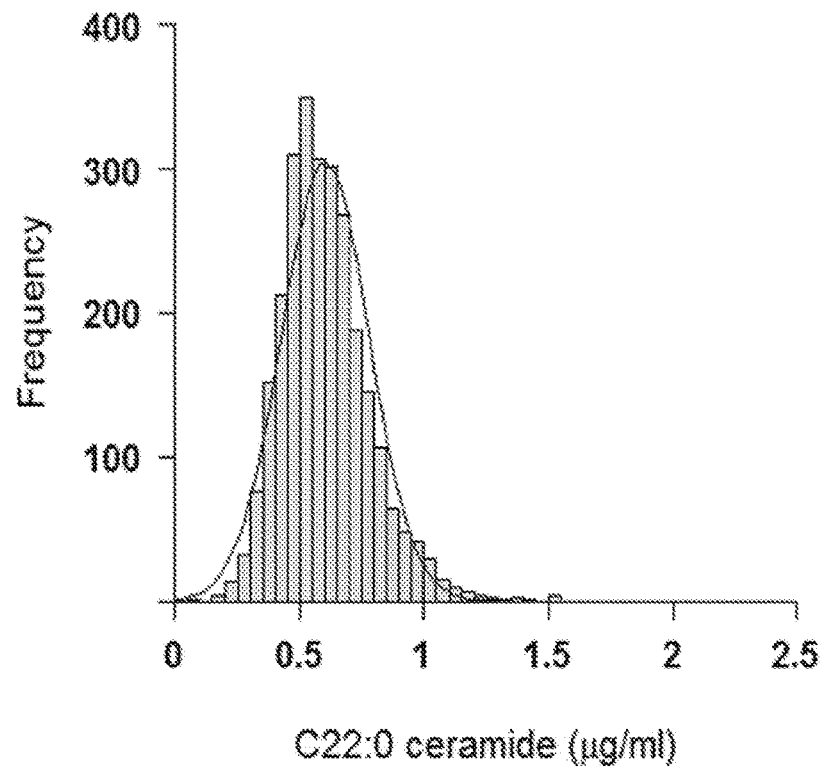
FIG. 4A, FIG. 4B, FIG. 4C and FIG. 4D depict graphs showing the distributions of plasma ceramides in FHS and SHIP.
Figure 4B:
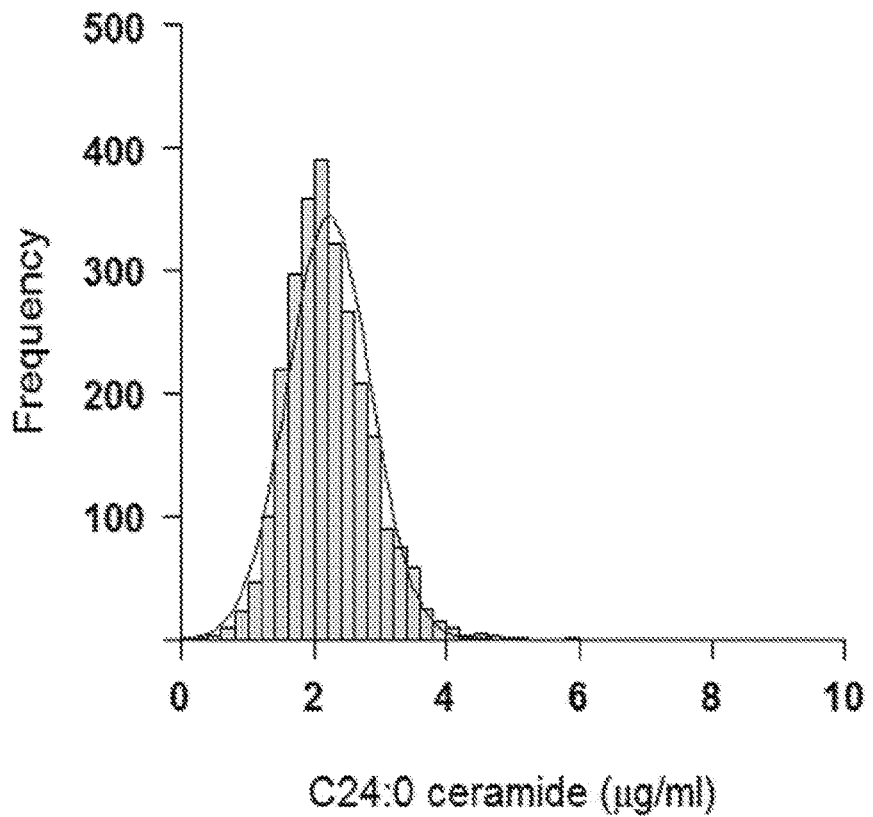
Figure 4C:
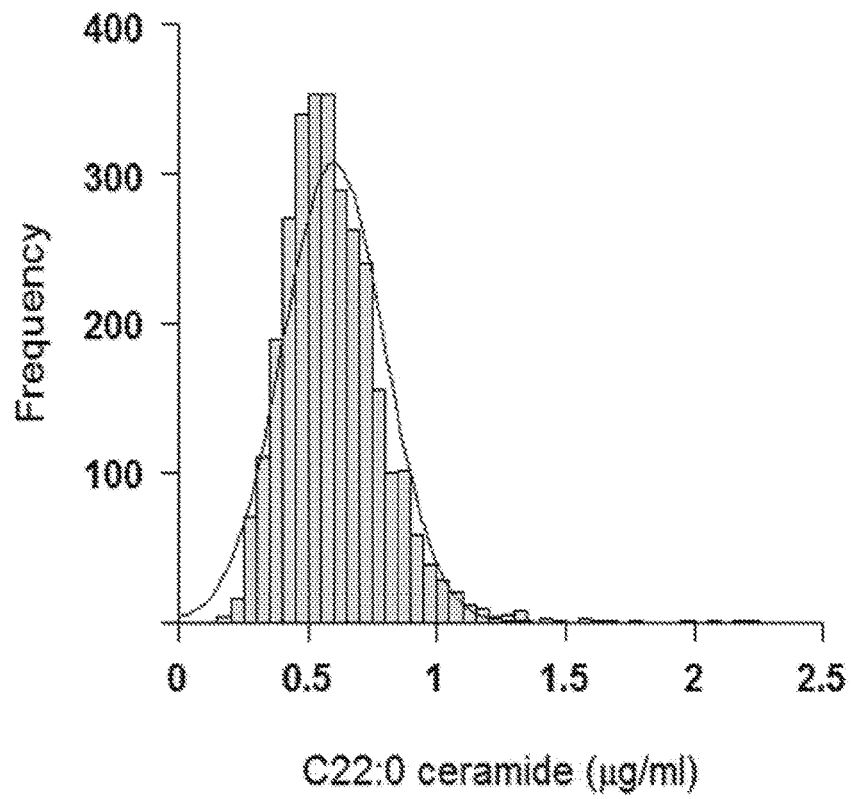
Figure 4D:
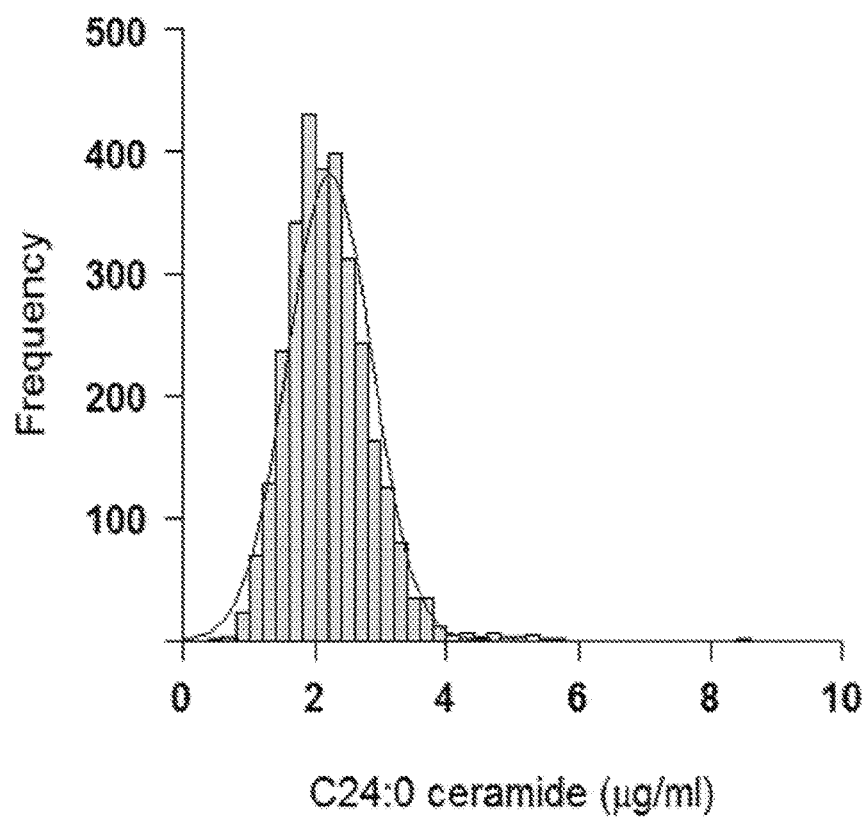

Plasma C22:0 and C24:0 ceramide levels were quantified in the offspring cohort of FHS. The baseline characteristics of the largest study sample in FHS are shown in Table 1. Overall, sample 1 was comprised of middle-aged to older individuals with >50% women. The plasma C22:0 and C24:0 ceramide values were normally distributed (FIG. 4A, FIG. 4B). C24:0 ceramide was nearly 4-fold more abundant than C22:0 ceramide with mean values of 2.2 µg/ml and 0.6 µg/ml, respectively (Table 1).

In multiple linear regression models, male sex, BMI, use of antihypertensive medication, and prior cardiovascular disease (CVD) were inversely associated with plasma levels of both ceramides, whereas systolic blood pressure (SBP) and total/HDL ratio were directly associated with both ceramide species (all P<0.01, Table 2). Age was inversely associated only with C24:0 ceramide. Smoking status and diabetes were not associated with either ceramide.

Example 2

Association Between Ceramides and Incidence of CVD, Coronary Heart Disease (CHD), Heart Failure (HF), and All-Cause Mortality in FHS There were 173 CVD, 89 CHD, and 92 HF events, as well as 240 deaths during a mean follow-up period of 5 years. Cumulative incidence of CVD, CHD, HF, and mortality decreased across ceramide tertiles are shown in FIG. 1A, FIG. 1B, FIG. 1C, FIG. 1D in FHS and Table 3. Correspondingly, higher levels of both ceramides were inversely associated with the incidence of CVD, CHD, and HF (P<0.05 for all), with the effect of C24:0 ceramide on the incidence of the corresponding event being stronger than that of C22:0 ceramide (FIG. 2A, FIG. 2B, FIG. 2C, FIG. 2D). A statistically significant association in FHS when investigating the association between ceramides and all-cause mortality was not found. The change in c-statistic for the prediction of CVD after adding ceramides to a model including standard CVD risk factors was minimal (Ac<0.01 for both ceramide types).

Example 3

Replication in Study of Health in Pomerania (SHIP)

In order to replicate these findings, C22:0 and C24:0 ceramide levels were also quantified in SHIP, another well-characterized population-based cohort. Baseline characteristics of the largest study sample in SHIP are shown in Table 4. Most characteristics were similar between SHIP sample A and FHS sample 1; however, the average age was lower and the percentage of smokers was higher in SHIP. The mean C22:0 and C24:0 ceramide levels were similar between SHIP and FHS. Associations between the ceramides and clinical correlates in SHIP were also similar to those observed in FHS (Table 5). In SHIP, there were 243 CVD, 205 CHD, and 128 HF events as well as 196 deaths during a mean follow-up period of 5.75 years. As in FHS, increased levels of both ceramides were inversely associated with the incidence of CVD, CHD, HF, and mortality, and the inverse associations of C24:0 ceramide with incident CHD and all-cause mortality were significant (FIG. 2A, FIG. 2B, FIG. 2C, FIG. 2D).

Example 4

Meta-Analysis

In meta-analyses, the proportion of total variability in effect size due to the between study variation was low to moderate, ranging from 0-72%, as indicated by the $I^2$-statistics (FIG. 2A, FIG. 2B, FIG. 2C, FIG. 2D). A statistically significant inverse association between C24:0 ceramide levels and incident CVD, CHD, and HF as well as with all-cause mortality was found. C22:0 ceramide levels were also inversely associated with CHD.

Discussion for the Examples

In the present investigation, it was observed that higher plasma levels of two very long chain ceramide species, C22:0 and C24:0, are associated with lower rates of incident CVD, CHD and HF over a mean follow up of five years among the FHS participants. Remarkably, in FHS every standard deviation increase of plasma C22:0 or C24:0 ceramide, corresponded to 19-33% lower hazards of developing clinical CVD, CHD, and HF, even after multivariable adjustment. The magnitude of decreased risk was largest for the more abundant plasma C24:0 ceramide. Consistent with these observations regarding incident CVD, it was found that C22:0 and C24:0 ceramide were inversely correlated with BMI (a known risk factor for CVD) and with prevalent CVD. We also found inverse correlations of the ceramides with CVD, CHD and HF in SHIP, a northern European community-based sample. Meta-analyses of the two studies confirmed the inverse association between C24:0 ceramide and CVD, CHD, and HF. Furthermore, meta-analyses revealed a significant inverse association between C24:0 ceramide and all-cause mortality. This investigation provides the first demonstration that specific ceramide molecular species in plasma are associated with incident CVD, CHD, and HF risk in the general population.

Ceramides play key roles in signaling pathways and stress responses in cellular and organ physiology. Yet, little is understood regarding the regulation of ceramide levels in the systemic circulation. De novo synthesized sphingolipids are secreted from hepatocytes with very low density lipoproteins. Ceramides are also generated extracellularly by sphingomyelinases secreted by macrophages, fibroblasts, and endothelial cells. The extent to which other tissues contribute to plasma ceramide levels is not known.

Past studies have uncovered a direct association between total plasma ceramides and CVD risk factors. In mice, genetic and pharmacological interventions that decrease total plasma ceramides improve insulin sensitivity and prevent progression to diabetes. In obese human participants with type 2 diabetes and insulin resistance, total ceramide is increased (Haus et al., *Diabetes* 2009;58:337-43 and de Mello et al., *Diabetologia* 2009;52:2612-5), and exercise training that improves glucose tolerance is accompanied by decreases in plasma ceramide (Kasumov et al., Improved insulin sensitivity after exercise training is linked to reduced plasma C14:0 ceramide in obesity and type 2 diabetes. *Obesity* (Silver Spring) 2015). In humans, increased total plasma ceramides have also been reported in hypertension, CHD, and HF (Spijkers et al., *PLoS One* 2011;6:e21817, Pan et al., *Coron Artery Dis* 2014;25:230-5 and Yu et al., *Can J Cardiol* 2015;31:357-63). Together, these studies suggest that total plasma ceramides reflect changes in lipid metabolism that would be expected to promote cardiovascular disease and mortality.

By contrast, it was found that C22:0 and C24:0 ceramides are inversely correlated with prevalent CVD cross-sectionally, and higher levels are associated with a striking reduction in the risk of CVD, CHD, and HF prospectively. In cardiac pathology associated with increased myocardial ceramides, low plasma levels could reflect the failure of diseased tissue to export the ceramides. Future studies are needed to dissect the mechanisms that regulate ceramide homeostasis between tissue and plasma pools.

These results expand the understanding of ceramide biology in several ways. A robust methodology was used to specifically quantify circulating concentrations of C22:0 and C24:0 ceramides in large community-based samples under continuous longitudinal surveillance for the development of CVD events. These results demonstrate that quantification of plasma C22:0 or C24:0 ceramide provides prognostic information in the general population that includes both men and women over a broad age range. These findings indicate that levels of these very long-chain ceramides may be decreased several years prior to the onset of clinical disease events.

Further, levels of these biomarkers may aid in discrimination of risk and investigations into the pathophysiology of CVD, CHD and HF, as well as identification of new therapeutic targets.

Methods for the Examples

FHS Study Samples.

The present investigation evaluated participants from the Framingham Heart Study (FHS) Offspring Cohort who attended their eighth examination cycle (2005-2008), when plasma concentrations of C22:0 and C24:0 ceramides were assayed. The Boston University Medical Center and Washington University Institutional Review Boards approved this study protocol, and all participants provided written informed consent.

Figure 3:
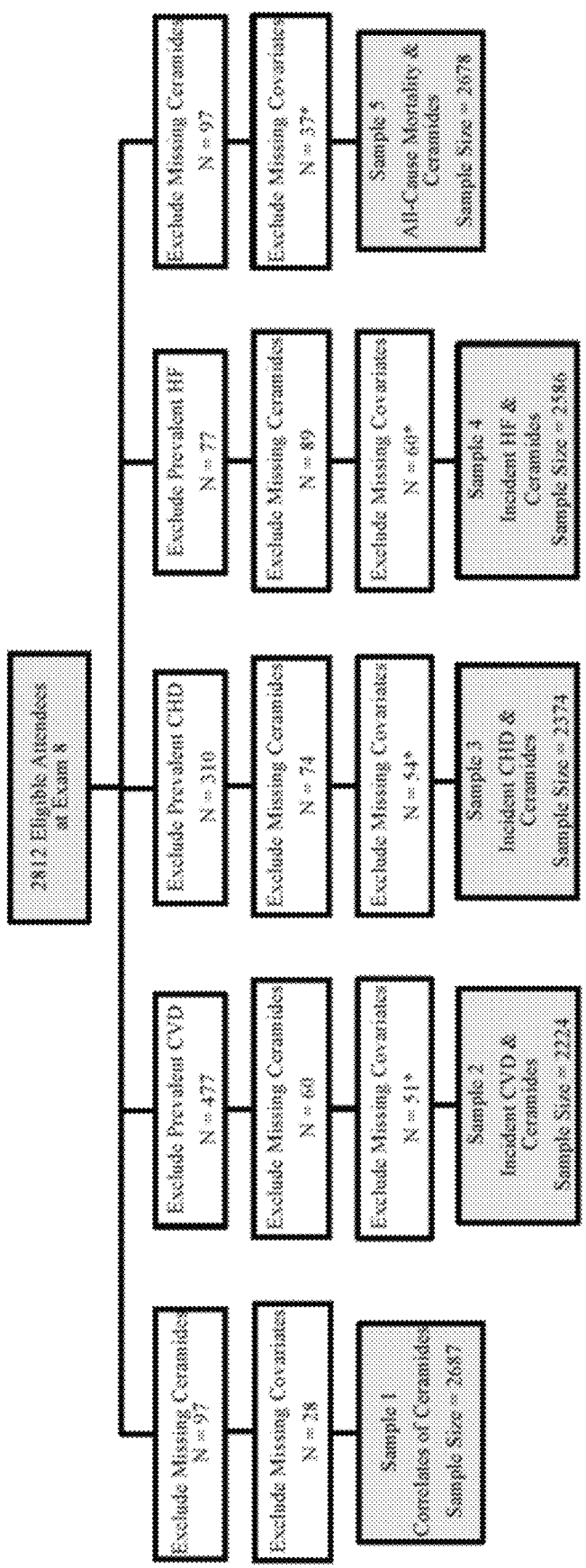
FIG. 3 depicts a schema delineating the generation of FHS samples. From 2,812 participants in the Offspring Cohort who attended their $8^{th}$ examination cycle, 5 participant samples were created based on availability of plasma samples and covariate data. For Samples 2, 3, and 4 individuals with prevalent cardiovascular disease (CVD, sample 2), coronary heart disease (CHD, sample 3) and heart failure (HF, sample 4) were excluded. *Individuals with missing follow-up time and/or plasma samples for analysis were also excluded at this stage.

From a total of 2,812 participants at the $8^{th}$ examination cycle, five different participant samples were used for analyses (FIG. 3). Sample 1 was used to examine clinical correlates of ceramides and excluded individuals who were missing plasma samples (N=97) or missing covariates (N=28), giving a final sample size of 2,687. From this, additional samples to examine outcomes of interest excluded those with prevalent disease of interest, all evaluated during follow-up through the end of 2012. Sample 2 (N=2,224) examined incident CVD, which includes fatal and non-fatal CHD, cerebrovascular disease (stroke or transient ischemic attack), peripheral arterial disease (intermittent claudication) and HF. Sample 3 (N=2,374) examined incident CHD, which includes myocardial infarction, coronary insufficiency, and angina pectoris. Sample 4 (N=2,586) examined incident HF. Sample 5 (N=2,678) examined all-cause mortality. Criteria for these events have been previously published (Kannel et al., Some risk factors related to the annual incidence of cardiovascular disease and death in pooled repeated biennial measurements: Framingham Heart Study, 30 year follow-up. In: Services HaH, ed. Bethesda, Md. 1987).

SHIP Study Samples.

With the aim of replicating the findings in FHS, data from the first cohort of the Study of Health in Pomerania (SHIP) was used (Dorr et al., *J Clin Endocrinol Metab* 2005;90: 673-7). The Institutional Review Board approved this study protocol, and all participants provided written informed consent. CVD, CHD, and HF events were evaluated between SHIP-1 (2002-2006) and SHIP-2 (2008-2012), while mortality was tracked from SHIP-1 through the most recent mortality survey in November 2012. From the 3,300 participants who attended SHIP-1, when plasma ceramides were assayed, 96 were excluded for missing ceramide values and 157 were removed for missing covariates, yielding Sample A (N=3,047). Sample A was used to assess clinical correlates and association between ceramides and all-cause mortality during follow-up after the SHIP-1 examination. Three additional SHIP samples were created from the 2,223 participants who also attended SHIP-2, when CVD, CHD, and HF status was reassessed. These samples mirror samples 2, 3, and 4 in the FHS analysis with exclusions for prevalent disease of interest or unknown disease status at SHIP-1 or SHIP-2 examinations, missing ceramide values, or missing covariates. Sample B examined CVD (N=1,651), Sample C examined CHD (N=1,856), and Sample D examined HF (N=1,827).

Quantification of Ceramides.

A liquid chromatography-tandem mass spectrometry (LC-MS/MS) assay was used to quantify C22:0 and C24:0 ceramides in frozen fasting plasma samples (Jiang et al., *Anal Bioanal Chem* 2013;405:7357-65). Each clinical sample analytical run included an 8-point calibration curve in duplicate, blank, blank with internal standard, and low, medium and high quality control (QC) samples. The total number of QC samples was at least 5% of that of unknown clinical samples. Samples that exceeded the highest standard were diluted and re-assayed. In the dilution sample re-assay, a dilution QC sample in triplicate was also included in the analytical run. The LC-MS/MS run acceptance criteria included: 1) a minimum of six standards within ±15%, except for the lowest standard for which ±20% of the nominal value was accepted; 2) at least 67% of the QC samples within 15% of their respective nominal values; and 3) not all replicates at the same level of QC outside ±15% of the nominal value (Guidance for Industry: Bioanalytical Method Validations. 2001. www.fda.gov/downloads/Drugs/Guidances/ucm070107.pdf). The analysis for FHS and SHIP samples was performed in 14 and 11 batches, respectively. All batches met acceptance criteria. In addition, five percent of FHS samples were analyzed in duplicate. Mean inter-assay coefficient of variation for duplicate samples for C22:0 and C24:0 ceramide were 1.56% and 1.66%, respectively.

Statistical Analysis.

Utilizing data from FHS sample 1 participants, multiple linear regression models to assess the correlates of C22:0 and C24:0 ceramide levels (separate models for each lipid) were implemented. In these models, ceramide levels served as the dependent variable, and age, sex, body mass index (BMI), systolic blood pressure (SBP), antihypertensive medications, smoking status, diabetes, and the ratio of total to HDL cholesterol served as independent variables. These models were also adjusted for prevalent CVD. Data from participants in samples 2, 3, 4, and 5 was then used to perform Cox proportional hazards regression analysis, evaluating the relationship between both ceramide species and CVD, CHD, HF, and all-cause mortality (separate models for each event type and ceramide species) after confirming that the proportionality of hazards assumption had been met. All multivariable models were adjusted for age, sex, BMI, SBP, diabetes, smoking status, use of anti-hypertensive medications, and the ratio of total to HDL cholesterol. All-cause mortality models were additionally adjusted for prevalent CVD. Furthermore, cumulative incidence plots were created to assess the incidence of events by ceramide tertile. Incremental effect of ceramides over standard CVD risk factors was assessed in FHS sample 2 by examining the change in c-statistics.

As a supplementary investigation, analyses were repeated using SHIP samples A, B, C, and D. Cox proportional hazards regression models were used to examine the association between ceramides and all-cause mortality, since exact death dates were known. For non-fatal events, the midpoint between an individual's SHIP-1 and SHIP-2 dates was used as the follow-up time. To accommodate the ties due to interval censoring when modeling the association between ceramides and each of CVD, CHD, and HF, piecewise constant hazard models with a Poisson distribution and an offset equal to the log follow-up time were used. All models were adjusted for the same set of covariates used for FHS analyses.

Meta-analyses were performed using FHS and SHIP samples. Values of $I^2$ were calculated for each association to determine the degree of heterogeneity among the results. Maximum Likelihood Random Effects models were then used in the meta-analyses to account for the moderate heterogeneity indicated by the values of $I^2$. Statistical significance was assessed using a P-value of <0.05. All FHS and meta-analyses were performed using SAS software version 9.3. (Cary, N.C.), while all SHIP analyses were performed using Stata version 13.1 (Stata Corp. 2013).

TABLE 1

Descriptive characteristics of largest study sample in FHS (Sample 1)

| Characteristics | N = 2687 |
|---|---|
| Age, Years | 66.3 ± 8.9 |
| Men, % | 45.6 |

TABLE 1-continued

Descriptive characteristics of largest study sample in FHS (Sample 1)

| Characteristics | N = 2687 |
|---|---|
| Body Mass Index, kg/m$^2$ | 28.3 ± 5.4 |
| Systolic Blood Pressure, mm Hg | 128.4 ± 17.2 |
| Diastolic Blood Pressure, mm Hg | 73.4 ± 10.1 |
| Total Cholesterol, mg/dL | 186.1 ± 37.4 |
| HDL Cholesterol, mg/dL | 57.4 ± 18.2 |
| Fasting Glucose, mg/dL | 106.7 ± 23.8 |
| C22:0 Ceramide, µg/ml | 0.6 ± 0.2 |
| C24:0 Ceramide, µg/ml | 2.2 ± 0.6 |
| Hypertension, % | 58.4 |
| Antihypertensive Medication use, % | 48.6 |
| Lipid Lowering Medication use, % | 45.0 |
| Diabetes mellitus, % | 13.7 |
| Smokers, % | 8.9 |

Values are mean ± SD for continuous variables

TABLE 2

Clinical correlates of plasma ceramide concentrations in FHS.

| Variable | β Estimate | P-value |
|---|---|---|
| C22:0 Ceramide | | |
| Age | 0.00003 | 0.9345 |
| Male | −0.0723 | <0.0001 |
| Body Mass Index | −0.0018 | 0.0019 |
| Systolic Blood Pressure | 0.0007 | <0.0001 |
| Antihypertensive Medication | −0.0426 | <0.0001 |
| Smoking Status | 0.0080 | 0.4351 |
| Diabetes Status | 0.0104 | 0.2453 |
| Total/HDL Cholesterol | 0.0846 | <0.0001 |
| Prevalent CVD | −0.0367 | <0.0001 |
| C24:0 Ceramide | | |
| Age | −0.0064 | <0.0001 |
| Male | −0.1570 | <0.0001 |
| Body Mass Index | −0.0164 | <0.0001 |
| Systolic Blood Pressure | 0.0034 | <0.0001 |
| Antihypertensive Medication | −0.1532 | <0.0001 |
| Smoking Status | −0.0147 | 0.7032 |
| Diabetes Status | −0.0392 | 0.2435 |
| Total/HDL Cholesterol | 0.2177 | <0.0001 |
| Prevalent CVD | −0.1508 | <0.0001 |

Multiple linear regression models were used, where ceramides served as dependent variables and clinical correlates served as independent variables; beta estimates represent the per-unit increase in ceramide levels for continuous variables and presence (vs. absence) for dichotomous variables.

TABLE 3

Incidence rates of outcomes by tertiles of ceramide

| Incident Event | Ceramide Tertile[1] | Number of events Number at risk | Person-Years | Incidence Rate[2] |
|---|---|---|---|---|
| C22:0 Ceramide | | | | |
| CVD | 1 | 62/733 | 3328 | 1.86 |
| | 2 | 55/7289 | 3280 | 1.68 |
| | 3 | 56/763 | 3520 | 1.59 |
| CHD | 1 | 33/780 | 3611 | 0.91 |
| | 2 | 24/783 | 3600 | 0.67 |
| | 3 | 32/811 | 3826 | 0.84 |
| HF | 1 | 39/850 | 3916 | 1.00 |
| | 2 | 30/856 | 3931 | 0.76 |
| | 3 | 23/880 | 4102 | 0.56 |
| All-Cause Mortality | 1 | 96/877 | 5291 | 1.81 |
| | 2 | 80/883 | 5329 | 1.50 |
| | 3 | 64/918 | 5659 | 1.13 |

TABLE 3-continued

Incidence rates of outcomes by tertiles of ceramide

| Incident Event | Ceramide Tertile[1] | Number of events Number at risk | Person-Years | Incidence Rate[2] |
|---|---|---|---|---|
| C24:0 Ceramide | | | | |
| CVD | 1 | 75/730 | 3331 | 2.25 |
|  | 2 | 47/732 | 3324 | 1.41 |
|  | 3 | 51/762 | 3472 | 1.47 |
| CHD | 1 | 38/773 | 3615 | 1.05 |
|  | 2 | 26/785 | 3618 | 0.72 |
|  | 3 | 25/816 | 3804 | 0.66 |
| HF | 1 | 42/839 | 3919 | 1.07 |
|  | 2 | 31/859 | 3927 | 0.79 |
|  | 3 | 19/888 | 4104 | 0.46 |
| All-Cause Mortality | 1 | 98/883 | 5363 | 1.83 |
|  | 2 | 78/880 | 5325 | 1.46 |
|  | 3 | 64/915 | 5591 | 1.14 |

[1]Tertile 1 includes participants whose ceramide levels are less than or equal to the 33$^{rd}$ percentile. Tertile 2 includes participants whose ceramide levels are between the 33$^{rd}$ and 66$^{th}$ percentile. Tertile 3 includes participants whose ceramide levels are greater than or equal to the 66$^{th}$ percentile.
[2]Incidence Rate is per 100 person-years (i.e. the number of events among 100 people over the course of one year)

TABLE 4

Descriptive characteristics of largest study sample in SHIP (Sample A)

| Characteristics | N = 3047 |
|---|---|
| Age, Years | 53.9 ± 15.0 |
| Men, % | 47.8 |
| Body Mass Index, kg/m$^2$ | 28.0 ± 5.0 |
| Systolic Blood Pressure, mm Hg | 132.1 ± 19.4 |
| Diastolic Blood Pressure, mm Hg | 81.4 ± 10.5 |
| Total Cholesterol, mg/dL | 214.5 ± 45.0 |
| HDL Cholesterol, mg/dL | 45.5 ± 16.3 |
| C22:0 Ceramide, µg/ml | 0.6 ± 0.2 |
| C24:0 Ceramide, µg/ml | 2.2 ± 0.6 |
| Hypertension, % | 64.1 |
| Antihypertensive Medication use, % | 41.2 |
| Lipid Lowering Medication use, % | 14.9 |
| Diabetes mellitus, % | 12.4 |
| Smokers, % | 26.0 |

Values are mean ± SD for continuous variables

TABLE 5

Clinical correlates of plasma ceramide concentrations in SHIP.

| Variable | β Estimate | P-value |
|---|---|---|
| C22:0 Ceramide | | |
| Age | 0.0011 | <0.001 |
| Male | −0.0617 | <0.001 |
| Body Mass Index | 0.0009 | 0.154 |
| Systolic Blood Pressure | 0.0010 | <0.001 |
| Antihypertensive Medication | −0.0197 | 0.008 |
| Smoking Status | 0.0224 | 0.001 |
| Diabetes Status | −0.0034 | 0.716 |
| Total/HDL Cholesterol | 0.0510 | <0.001 |
| Prevalent CVD | −0.0098 | 0.170 |
| C24:0 Ceramide | | |
| Age | 0.0030 | <0.001 |
| Male | −0.0981 | <0.001 |
| Body Mass Index | −0.0109 | <0.001 |
| Systolic Blood Pressure | 0.0044 | <0.001 |
| Antihypertensive Medication | −0.1055 | <0.001 |
| Smoking Status | 0.0507 | 0.031 |
| Diabetes Status | −0.1035 | 0.001 |
| Total/HDL Cholesterol | 0.1468 | <0.001 |
| Prevalent CVD | −0.0597 | 0.015 |

Multiple linear regression models were used, where ceramides served as dependent variables and clinical correlates served as independent variables; beta estimates represent the per-unit increase in ceramide levels for continuous variables and presence (vs. absence) for dichotomous variables.

What is claimed is:

1. A method to determine a risk of cardiovascular disease (CVD) in a subject, the method comprising:
   providing or having been provided a biological sample from a subject having unknown CVD status;
   extracting ceramide 24:0, and optionally ceramide 22:0 from the biological sample by protein precipitation in a solution comprising isopropanol and chloroform, resulting in an extracted sample;
   injecting the extracted sample comprising a stable isotope internal standard into a liquid chromatography-mass spectrometer (LC-MS/MS) and measuring an amount of ceramide 24:0, and optionally ceramide 22:0 in the extracted sample;
   wherein,
      the extracted sample is separated by gradient LC comprising a mobile phase composition and a step gradient of the mobile phase composition over a period of about 5 min;
      the mobile phase composition comprises solvent B comprising about 0.1% formic acid in isopropanol and, optionally, solvent A comprising about 0.1 formic acid in water; and
      the step gradient comprises
         (a) holding the mobile phase composition comprising about 65% solvent B and about 35% solvent A constant for about 0.5 min;
         (b) changing the mobile phase composition comprising about 65% solvent B and about 35% solvent A to about 90% solvent B and about 10% solvent A over a step gradient time of about 1.5 min;
         (c) changing the mobile phase composition comprising about 90% solvent B and about 10% solvent A to about 100% solvent B over the step gradient time of about 0.1 min;
         (d) holding the mobile phase composition comprising about 100% solvent B constant for about 0.9 min;
         (e) changing the mobile phase composition comprising about 100% solvent B to about 65% solvent B and about 35% solvent A over the step gradient time of about 0.1 min; and
         (f) holding the mobile phase composition comprising about 65% solvent B and about 35% solvent A for about 1.9 min;
   comparing the amount of ceramide 24:0 in the biological sample to a reference value of ceramide 24:0, and optionally comparing the amount of ceramide 22:0 in the biological sample to a reference value of ceramide 22:0; and
   classifying the subject as at highest risk for CVD if the amount of ceramide 24:0 is less than the reference value of ceramide 24:0 of 1.97 µg/ml, and optionally ceramide 22:0 is less than the reference value of ceramide 22:0 of 0.523 µg/ml;

classifying the subject as at lower risk for CVD if the amount of ceramide 24:0 is less than the reference value of ceramide 24:0 of 2.45 µg/ml, and optionally ceramide 22:0 is less than the reference value of ceramide 22:0 of 0.659 µg/ml; or classifying the subject as at least risk for CVD if the amount of ceramide 24:0 is greater than the reference value of ceramide 24:0 of 2.45 µg/ml, and optionally ceramide 22:0 is greater than the reference value of ceramide 22:0 of 0.659 µg/ml.

2. The method of claim 1, wherein the subject has no risk factors for CVD.

3. The method of claim 1, wherein the subject has one or more risk factors for CVD.

4. The method of claim 3, wherein the one or more risk factors is selected from the group consisting of male gender, body mass index (BMI), high blood pressure, prior CVD, high cholesterol, and age.

5. The method of claim 1, wherein the CVD is coronary heart disease (CHD) or heart failure (HF).

6. The method of claim 5, wherein the CHD is selected from the group consisting of myocardial infarction (MI), coronary insufficiency, and angina pectoris.

7. The method of claim 1, wherein the CVD is selected from the group consisting of fatal and non-fatal coronary heart disease (CHD), cerebrovascular disease, peripheral arterial disease, and heart failure.

8. The method of claim 1, wherein
the biological sample is blood, plasma, or serum.

9. The method of claim 1, wherein both ceramide 24:0 and ceramide 22:0 are measured.

10. A method to prevent cardiovascular disease (CVD) in a subject with unknown CVD status, the method comprising:
    providing or having been provided a biological sample from a subject having unknown CVD status;
    extracting ceramide 24:0, and optionally ceramide 22:0 from the biological sample by protein precipitation in a solution comprising isopropanol and chloroform, resulting in an extracted sample;
    injecting the extracted sample comprising a stable isotope internal standard into a liquid chromatography-mass spectrometer (LC-MS/MS) and measuring an amount of ceramide 24:0, and optionally ceramide 22:0 in the extracted sample;
    wherein,
        the extracted sample is separated by gradient LC comprising a mobile phase composition and a step gradient of the mobile phase composition over a period of about 5 min;
        the mobile phase composition comprises solvent B comprising about 0.1% formic acid in isopropanol and, optionally, solvent A comprising about 0.1% formic acid in water; and
        the step gradient comprises
            (a) holding the mobile phase composition comprising about 65% solvent B and about 35% solvent A constant for about 0.5 min;
            (b) changing the mobile phase composition comprising about 65% solvent B and about 35% solvent A to about 90% solvent B and about 10% solvent A over a step gradient time of about 1.5 min;
            (c) changing the mobile phase composition comprising about 90% solvent B and about 10% solvent A to about 100% solvent B over the step gradient time of about 0.1 min;
            (d) holding the mobile phase composition comprising about 100% solvent B constant for about 0.9 min;
            (e) changing the mobile phase composition comprising about 100% solvent B to about 65% solvent B and about 35% solvent A over the step gradient time of about 0.1 min; and
            (f) holding the mobile phase composition comprising about 65% solvent B and about 35% solvent A for about 1.9 min;
    comparing the amount of ceramide 24:0 in the biological sample to a reference value of ceramide 24:0, and optionally comparing the amount of ceramide 22:0 in the biological sample to a reference value of ceramide 22:0;
    classifying the subject as at highest risk for CVD if the amount of ceramide 24:0 is less than the reference value of ceramide 24:0 of 1.97 µg/ml, and optionally ceramide 22:0 is less than the reference value of ceramide 22:0 of 0.523 µg/ml;
    classifying the subject as at lower risk for CVD if the amount of ceramide 24:0 is less than the reference value of ceramide 24:0 of 2.45 µg/ml, and optionally ceramide 22:0 is less than the reference value of ceramide 22:0 of 0.659 µg/ml; or
    classifying the subject as at least risk for CVD if the amount of ceramide 24:0 is greater than the reference value of ceramide 24:0 of 2.45 µg/ml, and optionally ceramide 22:0 is greater than the reference value of ceramide 22:0 of 0.659 µg/ml; and
    treating the subject to prevent future CVD events when the subject is at highest risk or lower risk for CVD.

11. The method of claim 10, wherein the subject has no history of CVD.

12. The method of claim 10, wherein the subject has a history of CVD.

13. The method of claim 10, wherein the CVD is selected from the group consisting of fatal coronary heart disease (CHD), non-fatal CHD, cerebrovascular disease, peripheral arterial disease, and heart failure.

14. The method of claim 13, wherein the fatal or non-fatal CHD is selected from the group consisting of myocardial infarction (MI), coronary insufficiency, and angina pectoris.

15. The method of claim 10, wherein treating the subject to prevent future CVD events comprises:
    stress reduction;
    diet changes comprising lowering sodium and trans fat consumption or increasing intake of fresh fruits and vegetables, whole unprocessed high-fiber grains, or healthy sources of fats and proteins;
    lifestyle changes comprising cessation of smoking, exercising, alcohol in moderation, mediation, progressive relaxation, yoga, or biofeedback training;
    intervention or surgery comprising balloon angioplasty and stents, balloon valvuloplasty, heart bypass surgery, open heart surgery, pacemaker or defibrillator implantation, heart transplantation, cardioversion, atrial fibrillation and bypass tract ablation, or left ventricular assist device (LVAD); or
    administration of aspirin, ACE inhibitors, angiotensin II receptor blockers, anti-arrhythmics, beta-blockers, high blood pressure medication, high cholesterol medication, diuretics, water pills, calcium channel blocker drugs, thrombolytic drugs, digoxin, nitrates, hydralazine, antiplatelet drugs, blood thinners, or corticosteroids.

16. A method for monitoring cardiovascular disease (CVD) in a subject, the method comprising:
   measuring a first amount of ceramide 24:0, and optionally a first amount of ceramide 22:0, in a biological sample obtained from the subject;
   classifying the subject as at a highest risk, a lower risk or at least risk of CVD; wherein
   the subject is classified as at highest risk for CVD if the first amount of ceramide 24:0 is less than a reference value of ceramide 24:0 of 1.97 µg/ml, and optionally the first amount of ceramide 22:0 is less than a reference value of ceramide 22:0 of 0.523 µg/ml;
   the subject is classified as at lower risk for CVD if the first amount of ceramide 24:0 is less than a reference value of ceramide 24:0 of 2.45 µg/ml, and optionally the first amount of ceramide 22:0 is less than a reference value of ceramide 22:0 of 0.659 µg/ml; or
   the subject is classified as at least risk for CVD if the first amount of ceramide 24:0 is greater than a reference value of ceramide 24:0 of 2.45 µg/ml, and optionally the first amount of ceramide 22:0 is greater than a reference value of ceramide 22:0 of 0.659 µg/ml; and
   then at a later time, treating the subject to prevent future CVD events when the subject is classified to be at the highest risk or at the lower risk for CVD and measuring a second amount of ceramide 24:0, and optionally a second amount of ceramide 22:0, in a biological sample obtained from the subject,
   wherein a change in the second amount of ceramide 24:0, and optionally ceramide 22:0, from the first amount indicates a change in risk of the subject developing cardiovascular disease (CVD) over time,
wherein measuring the first amount of ceramide 24:0, and optionally the first amount of ceramide 22:0 and measuring the second amount of ceramide 24:0, and optionally the second amount of ceramide 22:0 comprises
   providing or having been provided a biological sample from the subject:
   extracting ceramide 24:0, and optionally ceramide 22:0 from the biological sample by protein precipitation in a solution comprising isopropanol and chloroform, resulting in an extracted sample;
   injecting the extracted sample comprising a stable isotope internal standard into a liquid chromatography-mass spectrometer (LC-MS/MS) and measuring an amount of ceramide 24:0, and optionally ceramide 22:0 in the extracted sample; wherein,
   the extracted sample is separated by gradient LC comprising a mobile phase composition and a step gradient of the mobile phase composition over a period of about 5 min;
   the mobile phase composition comprises solvent B comprising about 0.1% formic acid in isopropanol and, optionally, solvent A comprising about 0.1% formic acid in water; and
   the step gradient comprises
   (a) holding the mobile phase composition comprising about 65% solvent B and about 35% solvent A constant for about 0.5 min;
   (b) changing the mobile phase composition comprising about 65% solvent B and about 35% solvent A to about 90% solvent B and about 10% solvent A over a step gradient time of about 1.5 min;
   (c) changing the mobile phase composition comprising about 90% solvent B and about 10% solvent A to about 100% solvent B over the step gradient time of about 0.1 min;
   (d) holding the mobile phase composition comprising about 100% solvent B constant for about 0.9 min;
   (e) changing the mobile phase composition comprising about 100% solvent B to about 65% solvent B and about 35% solvent A over the step gradient time of about 0.1 min; and
   (f) holding the mobile phase composition comprising about 65% solvent B and about 35% solvent A for about 1.9 min.

17. The method of claim 16, wherein an increase in the second amount of ceramide 24:0 compared to the first amount of ceramide 24:0, and optionally an increase in the second amount of ceramide 22:0 compared to the first amount of ceramide 22:0, indicates an abatement of disease progression and a decrease in the second amount of ceramide 24:0 compared to the first amount of ceramide 24:0, and optionally a decrease in the second amount of ceramide 22:0 compared to the first amount of ceramide 22:0, indicates disease progression.

18. The method of claim 17, wherein the treatment comprises a first treatment and, optionally, a second treatment; and
   when disease progression is indicated, the subject is administered the second treatment; or
   the method is used to determine a response to the first treatment.

19. The method of claim 18, wherein if the second amount of ceramide 24:0 increases compared to the first amount of ceramide 24:0, and optionally the second amount of ceramide 22:0 increases compared to the first amount of ceramide 22:0, then the subject is responding to the first treatment and if the second amount of ceramide 24:0 decreases or remains the same as the first amount of ceramide 24:0, and optionally the second amount of ceramide 22:0 decreases or remains the same as the first amount of ceramide 22:0, then the subject is not responding to the first treatment.

20. The method of claim 18, wherein the first treatment or the second treatment comprises:
   stress reduction;
   diet changes comprising lowering sodium and trans fat consumption or increasing intake of fresh fruits and vegetables, whole unprocessed high-fiber grains, or healthy sources of fats and proteins;
   lifestyle changes comprising cessation of smoking, exercising, alcohol in moderation, mediation, progressive relaxation, yoga, or biofeedback training;
   intervention or surgery comprising balloon angioplasty and stents, balloon valvuloplasty, heart bypass surgery, open heart surgery, pacemaker or defibrillator implantation, heart transplantation, cardioconversion, atrial fibrillation and bypass tract ablation, or left ventricular assist device (LVAD); or
   administration of aspirin, ACE inhibitors, angiotensin II receptor blockers, anti-arrhythmics, beta-blockers, high blood pressure medication, high cholesterol medication, diuretics, water pills, calcium channel blocker drugs, thrombolytic drugs, digoxin, nitrates, hydralazine, antiplatelet drugs, blood thinners, or corticosteroids.

21. The method of claim 16, wherein an increase in the second amount of ceramide 24:0 compared to the first amount of ceramide 24:0, and optionally an increase in the second amount of ceramide 22:0 compared to the first amount of ceramide 22:0, indicates a decreased risk of disease progression and a decrease in the second amount of ceramide 24:0 compared to the first amount of ceramide 24:0, and optionally a decrease in the second amount of ceramide 22:0 compared to the first amount of ceramide 22:0, indicates an increased risk of disease progression.

22. The method of claim 21, wherein the treatment comprises a first treatment and optionally, a second treatment; and
   when an increased risk of disease progression is indicated, the subject is administered the second treatment; or
   the method is used to determine a response to the first treatment.

23. The method of claim 22, wherein if the second amount of ceramide 24:0 increases compared to the first amount of ceramide 24:0, and optionally the second amount of ceramide 22:0 increases compared to the first amount of ceramide 22:0, then the subject is responding to the first treatment and if the second amount of ceramide 24:0 decreases or remains the same as the first amount of ceramide 24:0, and optionally the second amount of ceramide 22:0 decreases or remains the same as the first amount of ceramide 22:0, then the subject is not responding to the first treatment.

24. The method of claim 16, wherein
   the biological sample is blood, plasma, or serum.

* * * * *